US008216699B2

(12) United States Patent
Burn et al.

(10) Patent No.: US 8,216,699 B2
(45) Date of Patent: *Jul. 10, 2012

(54) ORGANIC PHOSPHORESCENT MATERIAL AND ORGANIC OPTOELECTRONIC DEVICE

(75) Inventors: Paul Leslie Burn, Oxford (GB); Ifor David William Samuel, Fife (GB); Shih-Chun Lo, Oxford (GB)

(73) Assignee: Isis Innovation Limited, Oxford (GB)

( * ) Notice: Subject to any disclaimer, the term of this patent is extended or adjusted under 35 U.S.C. 154(b) by 259 days.

This patent is subject to a terminal disclaimer.

(21) Appl. No.: 12/646,529

(22) Filed: Dec. 23, 2009

(65) Prior Publication Data

US 2010/0096983 A1  Apr. 22, 2010

Related U.S. Application Data

(62) Division of application No. 10/556,780, filed as application No. PCT/GB2004/002127 on May 17, 2004, now Pat. No. 7,659,010.

(30) Foreign Application Priority Data

May 16, 2003 (GB) .................................. 0311234.9

(51) Int. Cl.
*H01L 51/54* (2006.01)
(52) U.S. Cl. .. 428/690; 428/917; 313/504; 257/E51.044
(58) Field of Classification Search .................. None
See application file for complete search history.

(56) References Cited

U.S. PATENT DOCUMENTS

| 5,503,910 | A | * | 4/1996 | Matsuura et al. | ............ | 428/690 |
| 5,686,360 | A | | 11/1997 | Harvey et al. | | |
| 7,659,010 | B2 | * | 2/2010 | Burn et al. | .................... | 428/690 |
| 2001/0019782 | A1 | | 9/2001 | Igarashi et al. | | |
| 2002/0034656 | A1 | * | 3/2002 | Thompson et al. | ........... | 428/690 |
| 2002/0048689 | A1 | * | 4/2002 | Igarashi et al. | ............... | 428/690 |
| 2002/0055014 | A1 | | 5/2002 | Okada et al. | | |
| 2002/0134984 | A1 | | 9/2002 | Igarashi | | |
| 2006/0008670 | A1 | | 1/2006 | Lin et al. | | |

FOREIGN PATENT DOCUMENTS

| EP | 0880303 | A1 | 11/1998 |
| EP | 0949850 | A1 | 10/1999 |
| EP | 1175128 | A2 | 1/2002 |
| EP | 1211257 | A2 | 6/2002 |
| EP | 1239526 | A2 | 9/2002 |
| EP | 1245659 | A1 | 10/2002 |
| EP | 1311138 | A1 | 5/2003 |
| EP | 1348711 | A1 | 10/2003 |
| WO | 90/13148 | A1 | 11/1990 |
| WO | 97/42666 | A1 | 11/1997 |
| WO | 98/05187 | A1 | 2/1998 |
| WO | 00/36665 | A1 | 6/2000 |
| WO | 02/15645 | A1 | 2/2002 |
| WO | 02/23579 | A1 | 3/2002 |
| WO | 02/31896 | A2 | 4/2002 |
| WO | 02/060910 | A1 | 8/2002 |
| WO | 02/066552 | A1 | 8/2002 |
| WO | 02/066575 | A1 | 8/2002 |
| WO | 02/067343 | A1 | 8/2002 |
| WO | 02/068435 | A1 | 9/2002 |
| WO | 02/081488 | A1 | 10/2002 |
| WO | 02/093662 | A2 | 11/2002 |
| WO | 03/001616 | A2 | 1/2003 |
| WO | 03/040256 | A2 | 5/2003 |
| WO | 03/079736 | A1 | 9/2003 |
| WO | 2004/020448 | A1 | 3/2004 |

OTHER PUBLICATIONS

C.W. Tang, et al., Organic Electroluminescent Diodes, Applied Physics Letters 51 (12), Sep. 1987, 913-915.
M.A. Baldo, et al., Very High-efficiency Green Organic Light-emitting Devices Based on Electrophosphorescence, Applied Physics Letters 75 (1), Jul. 1999, 4-6.
M.G. Colombo, et al., Facial Tris Cyclometalated Rh3+ and Ir3+ Complexes . . . , Inorg. Chem. 1994, 33, 545-550.
R.J. Holmes, et al., Efficient, Deep-Blue Organic Electrophosphorescence by Guest Charge Trapping, Applied Physics Letters 82 (18), Nov. 2003, 3818-3820.
M. Ikai, et al., Highly Efficient Phosphorescence from Organic Light-Emitting Devices with an Exciton-Block Layer, Applied Physics Letters 79(2), Jul. 2001, 156-158.
International Search Report and Written Opinion Issued Under Date of Mailing of Oct. 18, 2004 in connection with PCT/GB2004/002127.
UK Search Report dated Oct. 7, 2003 in connection with GB 0311234.9.
U.S. Appl. No. 10/556,780 Office action dated Feb. 18, 2009.
U.S. Appl. No. 10/556,780 response to the Feb. 18, 2009 Office action.

* cited by examiner

*Primary Examiner* — Marie R. Yamnitzky
(74) *Attorney, Agent, or Firm* — Quarles & Brady, LLP

(57) ABSTRACT

The invention provides a cyclometallated complex comprising the structure of formula I

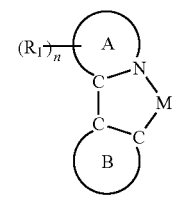

wherein:
M is a d-block transition metal;
B is a five- or six-membered aryl or heteroaryl ring which is optionally substituted and optionally fused to one or more other aryl or heteroaryl rings;
A is a five- or six-membered heteroaryl ring comprising at least three nitrogen atoms;
$R_1$ is a group other than hydrogen;
n is zero or an integer equal to or greater than one; and
A and B are optionally fused or linked by one or more covalent bonds.
The invention also provides the use of such complexes in optoelectronic devices, and in particular in organic light emitting devices.

34 Claims, 1 Drawing Sheet

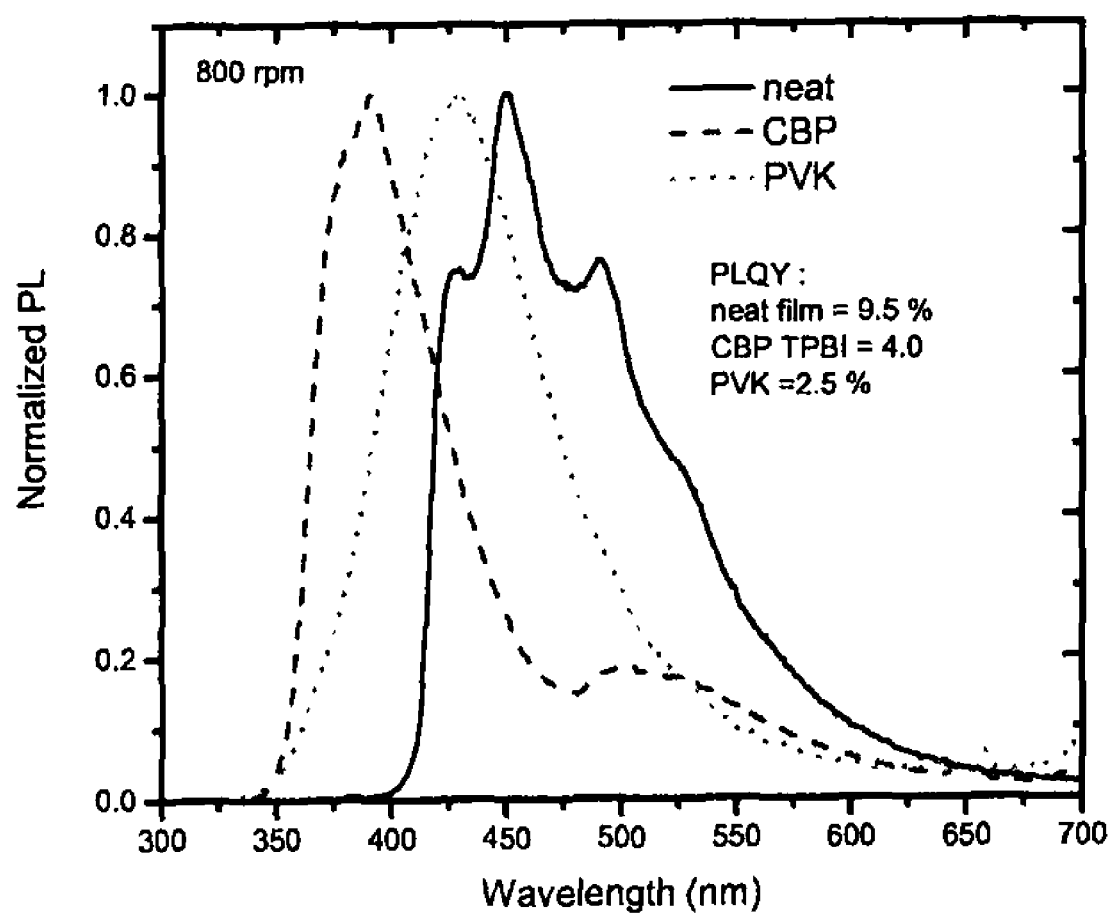

ORGANIC PHOSPHORESCENT MATERIAL AND ORGANIC OPTOELECTRONIC DEVICE

CROSS-REFERENCE TO RELATED APPLICATION

This application is a divisional of U.S. application Ser. No. 10/556,780 which was filed Aug. 24, 2006, now U.S. Pat. No. 7,659,010, and claims priority to International Patent Application PCT/GB2004/002127, filed May 17, 2004, which claims priority of Great Britain application 0311234.9 filed May 16, 2003. All applications are incorporated by reference herein.

FIELD OF INVENTION

The present invention relates to organic phosphorescent materials, in particular to blue organic phosphorescent materials and to organic electroluminescent devices comprising organic phosphorescent materials.

BACKGROUND OF THE INVENTION

Organic electroluminescent devices comprise a layer of organic electroluminescent material positioned between two electrodes. Application of a current between the two electrodes causes the organic material to electroluminescence. The phenomenon of organic electroluminescence has many applications in the fields of displays and lighting. In the late 1980's efficient organic electroluminescence was observed in conjugated polymers, as described in WO90/13148, and in complexes of aluminum 8-hydroxyquinolate, as described in Tang et al Applied Physics Letters 51, 913, (1987). The electroluminescence in such systems is termed fluorescence and is produced by radiative emission from the singlet excited states produced by the electrical excitation of the polymers or molecules. Much research over the last decade has been directed at the investigation of such fluorescent systems.

In the 1990s the efficient emission of light from the triplet excited states of electrically excited molecules was observed, Baldo et al Applied Physics Letters 75, 4, (1999). This electroluminescent system comprised a green light emitting cyclometallated iridium phenylpyridine complex and showed a higher efficiency than had previously been observed in fluorescent systems. This phenomenon, known as phosphorescence, has been widely investigated. US2002/0134984 discloses a series of iridium complexes in which iridium is coordinated to a bidentate ligand via two nitrogen atoms, such as compound 1 below. US2001/0019782 discloses a series of iridium complexes in which iridium is coordinated to a bidentate ligand, the ligand comprising two aryl moieties bonded by a C—N bond, such as compound 2 below. US2002/0055014 discloses a series of iridium complexes in which iridium is coordinated to a ligand comprising a phenylazole derivative, such as compound 3 below. WO02/15645 discloses the blue phosphorescent complex 4, known as Firpic, shown below.

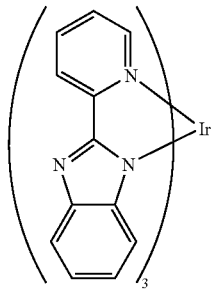

1

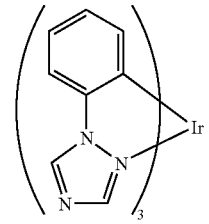

2

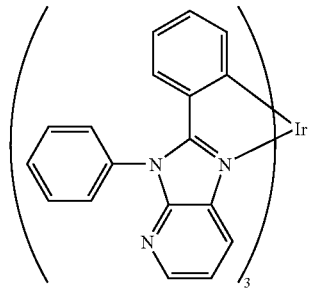

3

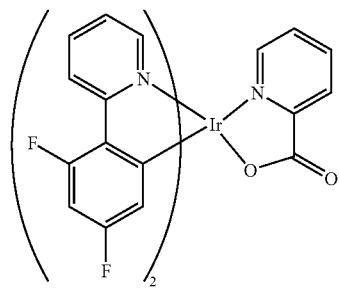

4

The cyclometallated phosphorescent complexes referred to above have been designed to be volatile to allow their deposition by vacuum evaporation. Vacuum evaporation is a technique commonly used to deposit layers of low molecular weight materials in the manufacture of electroluminescent devices. Other research has focussed on the incorporation of phosphorescent emitters into polymers, as disclosed in WO02/068435 and EP1245659. The incorporation of phosphorescent emitters into polymers allows the phosphorescent systems to be deposited using solution processing techniques such as ink-jet printing and screen printing. The advantage of using solution processing to produce electroluminescent displays has been widely recognised in the field, as disclosed for example in EP 0 880 303.

An alternative approach to provide solution processable phosphorescent materials has been to incorporate the phosphorescent emitters into dendrimers, as disclosed in WO02/066552. Dendrimers are highly branched macromolecules in which branched molecular sub-units, known as dendrons or dendrites, are attached to a core. The dendrimers disclosed in WO02/066552 comprise a cyclometallated phosphorescent core and a series of organic dendrons. The properties of such dendrimers make them ideal for solution processing. Further classes of electroluminescent dendrimers have been developed including dendrimers comprising dendrons based on aryl-aryl moieties, as disclosed in WO02/067343, and asymmetric dendrimers as disclosed in WO02/066575.

Much of the development of organic light emitting devices is aimed at the exploitation of these devices in display applications such as mobile phones and large area displays. Full colour displays require light emitting materials which emit light in the red, green and blue regions of the electromagnetic spectrum. Fluorescent organic materials capable of emitting red, green and blue light have been developed.

Phosphorescent materials emitting red and green light have been developed but there are relatively few examples of phosphorescent materials capable of emitting blue light. Although the above mentioned iridium complex Firpic emits blue light this is of a light blue colour rather than the deeper blue required for full colour displays.

As is clear from the above brief survey of recent research in the field there is a need for the development of phosphorescent compounds having a high efficiency and available in a range of colours suitable for use in display applications. In particular there is a need for a range of high efficiency phosphorescent complexes emitting light in the blue region of the electromagnetic spectrum. Further there is a need for a range of solution processable phosphorescent light emitting compounds.

SUMMARY OF THE INVENTION

The present invention provides phosphorescent light emitting compounds suitable for use in electroluminescent devices.

In a first embodiment the present invention provides a complex of formula I:

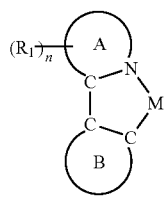

I wherein:
M is a d-block transition metal;
B is a five- or six-membered aryl or heteroaryl ring which is optionally substituted and optionally fused to one or more other aryl or heteroaryl rings;
A is a five- or six-membered heteroaryl ring comprising at least three nitrogen atoms;
$R_1$ is a group other than hydrogen;
n is zero or an integer equal to or greater than one; and
A and B are optionally fused or linked by one or more covalent bonds.

In a second embodiment the present invention comprises a cyclometallated complex comprising the structure of formula II:

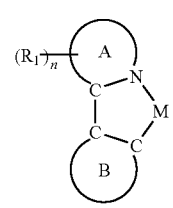

II wherein A is a five- or six-membered heteroaryl ring which comprises at least three heteroatoms and which is optionally substituted or fused, B is a five- or six-membered aryl or heteroaryl ring which is optionally substituted or fused, n is greater than one and $R_1$ is a dendron or a solubilising group.

In a third embodiment the present invention comprises a polymer comprising a cyclometallated complex comprising the structure of formula III:

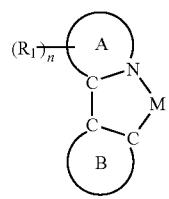

III wherein A is a five- or six-membered heteroaryl ring which comprises at least three heteroatoms and which is optionally substituted or fused, B is a five- or six-membered aryl or heteroaryl ring which is optionally substituted or fused, n is zero or greater than one and $R_1$ is a substituent other than hydrogen.

The present invention is also directed to an optoelectronic device comprising a cyclometallated complex of the present invention. In a preferred embodiment said optoelectronic device is an organic light emitting diode.

The present invention is further directed to an organic light emitting device comprising a blend comprising a cyclometallated complex according to the present invention and an organic host. Although not wishing to be bound by theory it is thought that the organic host acts as a charge transporter and a source of triplet excitons which are transferred to the light-emitting cyclometallated complex. Alternatively the recombination of the hole and electron charge carriers to form excitons may take place at the cyclometallated complex with the host acting as a charge transporter. Preferably the organic host comprises a carbazole moiety or a triarylamine moiety.

The present invention is also directed to the use of a cyclometallated complex according to the invention in an optoelectronic device.

The invention also provides an organic light-emitting device comprising an phosphorescent layer disposed between two electrodes, said phosphorescent layer, wherein said device has a CIE-y coordinate of less than 0.25.

BRIEF DESCRIPTION OF THE DRAWINGS

FIG. 1 shows the photoluminescent spectrum of a cyclometallated complex according to the present invention.

DESCRIPTION OF THE INVENTION

Unless otherwise stated, the term alkyl represents a linear or branched alkyl group or moiety which preferably contains from 1 to 6 carbon atoms such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a halogen is typically chlorine, fluorine, bromine or iodine. It is preferably chlorine, fluorine or bromine.

As used herein the term amino represents a group of formula —$NH_2$. The term $C_{1-6}$ alkylamino represents a group of formula —NHR' wherein R' is a $C_{1-6}$ alkyl group, preferably a $C_{1-4}$ alkyl group, as defined previously. The term di($C_{1-6}$ alkyl)amino represents a group of formula —NR'R" wherein R' and R" are the same or different and represent $C_{1-6}$ alkyl groups, preferably $C_{1-4}$ alkyl groups, as defined previously. As used herein the term amido represents a group of formula —$C(O)NH_2$.

As used herein, an aryl group is typically a $C_{6-10}$ aryl group such as phenyl or naphthyl. An aryl group may be unsubstituted or substituted at any position. Typically, it carries 0, 1, 2 or 3 substituents.

As used herein, references to an aryl group include fused ring systems in which an aryl group is fused to a carbocyclyl, heterocyclyl or heteroaryl group. The carbocyclyl, heterocyclyl or heteroaryl group to which the aryl group is fused may itself be fused to a further aryl, heteroaryl, carbocyclyl or heterocyclyl. Accordingly, the term aryl encompasses aryl groups such as phenyl when fused to other monocyclic or polycyclic ring systems. Exemplary fused ring systems include those where a phenyl ring is fused to a monocyclic carbocyclyl ring which is itself fused to a phenyl ring, for instance a carbazolyl group.

As used herein, a heteroaryl group is typically a 5- to 14-membered aromatic ring, such as a 5- to 10-membered ring, more preferably a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl, pyrazolyl, oxazolyl, isothiazolyl, benzofuranyl, isobenzofuranyl, benzothiophenyl, indolyl, indazolyl, carbazolyl, acridinyl, purinyl, cinnolinyl, quinoxalinyl, naphthyridinyl, benzimidazolyl, benzoxazolyl, quinolinyl, quinazolinyl and isoquinolinyl.

As used herein, references to a heteroaryl group include fused ring systems in which a heteroaryl group is fused to an aryl group. When the heteroaryl group is such a fused heteroaryl group, preferred examples are fused ring systems wherein a 5- to 6-membered heteroaryl group is fused to a phenyl group. Examples of such fused ring systems are benzofuranyl, isobenzofuranyl, benzothiophenyl, indolyl, indazolyl, benzimidazolyl, benzoxazolyl, quinolinyl, quinazolinyl and isoquinolinyl moieties.

A heteroaryl group may be unsubstituted or substituted at any position. Typically, it carries 0, 1, 2 or 3 substituents.

As used herein, an alkoxy group is typically a said alkyl group attached to an oxygen atom. A haloalkyl or haloalkoxy group is typically a said alkyl or alkoxy group substituted by one or more said halogen atoms. Typically, it is substituted by 1, 2 or 3 said halogen atoms. Haloalkyl and haloalkoxy groups include perhaloalkyl and perhaloalkoxy groups such as —$CX_3$ and —$OCX_3$ wherein X is a said halogen atom, for example chlorine or fluorine.

Ligands suitable for the cyclometallated complexes of the present invention comprise a five- or six-membered heteroaryl ring comprising at least three heteroatoms, termed A, and a five- or six-membered aryl or heteroaryl ring, termed B.

For the avoidance of doubt, while the cyclometallated complexes are shown in formulae I, II and III as bearing one ligand comprising rings A and B, the complexes may comprise further ligands which are not shown for the sake of clarity. For example, the complexes may comprise a further ligand of the same structure, i.e. a further ligand of structure:

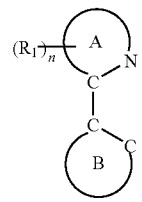

The complexes may alternatively or additionally comprise further ligands of a different structure. These options are discussed later in this description.

In the embodiment represented by formula I and the subsequent definition, A comprises at least three nitrogen atoms. According to one embodiment, there is provided a cyclometallated complex of formula I wherein M is a d-block transition metal, B is a five- or six-membered aryl or heteroaryl ring which is optionally substituted or fused, and either (i) A is a five membered heteroaryl ring comprising at least three nitrogen atoms, $R_1$ is a group other than hydrogen and n is equal to or greater than zero, or (ii) A is a six membered heteroaryl ring comprising at least three nitrogen atoms, $R_1$ is a group other than hydrogen and n is equal to or greater than two.

Rings A and B are linked by a carbon-carbon bond. Ring A comprises a nitrogen atom which coordinates to the metal of the cyclometallated complex. Ring B forms a carbon-metal sigma bond to the metal of the cyclometallated complex. In this way the central metal atom, the nitrogen on ring A, a carbon atom on ring B and the two carbon atoms which form the bond between rings A and B form a five-membered ring. Where ring A is a five-membered ring it may suitably be a triazole, an oxadiazole, a thiadiazole or a tetrazole. In addition to the carbon-carbon bond between rings A and B discussed above, the rings may also be fused or linked via one or more covalent bonds, as discussed below.

A is a 5- or 6-membered heteroaryl ring having at least three nitrogen atoms in the ring. The heteroaryl ring may be optionally substituted or fused to one or more aryl or heteroaryl groups. Suitable A groups therefore include triazoles, tetrazoles and triazines.

The A groups may also be substituted by one or more ketone or thioketone groups within the ring. Thus, suitable A groups include triazolones and triazolethiones, for example groups of the formula:

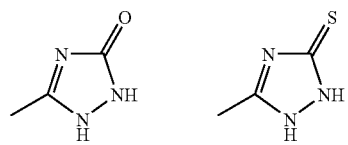

In the embodiment where A is a five-membered ring, A is preferably a triazole or tetrazole. In the embodiment where A is a six-membered ring, A is preferably a triazine. It is preferred that A is a five-membered ring.

Ring A may be unsubstituted or substituted by one or more $R_1$ groups. Suitable $R_1$ groups include halogen atoms and $C_{1-6}$ alkyl, aryl, $C_{1-6}$ alkoxy, amino, $C_{1-6}$ alkylamine, di($C_{1-6}$ alkyl)amino and carbazole groups. These substituents may themselves be substituted by, amongst other substituents, halogen atoms, $C_{1-6}$ alkyl groups and $C_{1-6}$ alkoxy groups.

Preferably at least one $R_1$ group on ring A is electron-donating. More preferably all $R_1$ substituents on ring A are electron-donating. Particularly preferred $R_1$ groups include $C_{1-6}$ alkoxy, $C_{1-6}$ alkyl, $C_{1-6}$ alkylamino, di($C_{1-6}$ alkyl)amino, aryl, carbazole, arylamino and diarylamino. Preferred $C_{1-6}$ alkoxy groups are $C_{1-4}$ alkoxy groups, for example methoxy or ethoxy. Preferred $C_{1-6}$ alkyl groups include ethyl, n-propyl, i-propyl, n-butyl, i-butyl and t-butyl. Preferred diarylamino groups include —NPhPh, wherein the phenyl rings may themselves be substituted by 1, 2 or 3 $C_{1-2}$ alkoxy groups.

In an alternative embodiment the $R_1$ groups may be electron-withdrawing groups, for example substituted by one or more halogen atom, haloalkyl groups (including perhaloalkyl groups such as perfluoroalkyl groups) or aryl groups.

Ring A may be further substituted. In a preferred embodiment heteroaryl ring A is substituted with at least one dendron. Such an embodiment may have a structure of the form CORE-[DENDRON]$_m$, in which CORE represents a cyclometallated complex according to the present invention, m represents an integer of 1 or more, each DENDRON, which may be the same or different, represents a dendritic molecular structure. Preferably said dendritic molecular structure comprises aryl and/or heteroaryl groups or nitrogen which are preferably connected by $sp^2$ or sp hybridised carbon atoms of said aryl or heteroaryl groups or via single bonds between N and said aryl or heteroaryl groups. CORE is defined as terminating in the single bond from ring A which is connected to an $sp^2$ hybridised ring carbon atom of the first aryl or heteroaryl group or nitrogen to which more than one dendritic branch is attached, said ring carbon atom or N forming part of said DENDRON. When present it is preferred that the DENDRON is attached to the CORE via a linking group, more preferably the linking group is a non-conjugated linking group such as an alkylene group, in particular a methylene or ethylene group.

n is preferably zero or an integer from 1 to 5, suitably 1 to 4. More preferably n is zero, one, two or three, most preferably one, two or three.

B is a 5- or 6-membered aryl or heteroaryl group. The aryl or heteroaryl group which may itself be substituted with or fused to one or more further aryl or heteroaryl groups.

When B is a 5- or 6-membered aryl group it is preferably selected from phenyl rings which are optionally fused to other aryl or heteroaryl groups. For example, suitable aryl groups include phenyl, phenanthrenyl, naphthyl, pyrenyl and fluorenyl groups. Most preferably B is a phenyl ring.

When B is a 5- or 6-membered heteroaryl group, the ring preferably comprises 1, 2 or 3 heteroatoms independently selected from oxygen, sulphur and nitrogen. Suitable heteroaryl groups include pyridine, pyrazine, pyrimidine, thiophene, furan and pyrrole, preferably pyridine, pyrazine and pyrimidine. These heteroaryl groups may optionally be fused to other aryl or heteroaryl groups, for example to a phenyl ring. For example, B may be a group selected from benzofuran, benzothiophene, benzoimidazole, indole, quinoline, isoquinoline, quinazoline.

The B group may be unsubstituted or substituted by one or more substituents. Suitable substituents include halogen atoms, $C_{1-6}$ alkyl, $C_{1-6}$ alkoxy, sulfoxides, sulfones, =O groups, aryl groups such as phenyl rings, and heteroaryl groups, wherein these substituents may themselves be substituted by one or more halogen atoms, $C_{1-4}$ alkyl, $C_{1-4}$ alkoxy, amino, $C_{1-4}$ alkylamino or di($C_{1-4}$ alkylamino) groups. Preferably the B group is substituted by at least one electron-withdrawing group such as a halogen atom, haloalkyl, haloalkoxy, sulfoxide or sulphone group. Preferred halogen atoms include bromine, chlorine and fluorine, more preferably chlorine and fluorine, and most preferably fluorine. Particularly preferred haloalkyl groups are fluoroalkyl groups. The alkyl group may be substituted in all positions by the halogen atoms, e.g. in order to form trifluoromethyl or —$CF_2CF_3$. Alternatively, the alkyl portion of the haloalkyl group may be substituted in only some positions, e.g. in order to form difluoromethyl or —$CFHCFH_2$. Preferred haloalkoxy groups include said haloalkyl groups which are linked via an oxygen atom, for example —$OCF_3$ or —$OCF_2CF_3$. Sulphoxide groups are groups of formula —$SO_2R'$ where R' is preferably hydrogen or a $C_{1-6}$ alkyl group. Sulphone groups are groups of formula —$SOR'$ where R' is preferably hydrogen or a $C_{1-6}$ alkyl group.

The B group is preferably substituted by one or more substituents, more preferably by one or two substituents. It is particularly preferred if the B group is substituted by two electron-withdrawing groups which are in the meta position relative to the point of attachment to the central metal atom M. Suitable substituents in these positions include fluorine and perfluorinated groups such as trifluoromethyl. The substituents may themselves be unsubstituted or substituted, for example with one or more $C_{1-4}$ alkyl, $C_{1-4}$ alkoxy, amino, $C_{1-4}$ alkylamino or di($C_{1-4}$ alkyl)amino groups.

Ring B may also be substituted by one or more dendrons. Such an embodiment may have a structure of the form CORE-[DENDRON]$_m$, in which CORE represents a cyclometallated complex according to the present invention, m represents an integer of 1 or more, each DENDRON, which may be the same or different, represents a dendritic molecular structure. Preferably said dendritic molecular structure comprises aryl and/or heteroaryl groups or nitrogen which are preferably connected by $sp^2$ or sp hybridised carbon atoms of said aryl or heteroaryl groups or via single bonds between N and said aryl or heteroaryl groups. CORE is defined as terminating in the single bond from ring B which is connected to an $sp^2$ hybridised ring carbon atom of the first aryl or heteroaryl group or nitrogen to which more than one dendritic branch is attached, said ring carbon atom or N forming part of said DENDRON. When present it is preferred that the DENDRON is attached to the CORE via a linking group, more preferably the linking group is a non-conjugated linking group such as an alkylene group, in particular a methylene or ethylene group.

Preferably said dendron comprises a carbazole moiety or a diarylamine or triarylamine moiety. Preferably said dendron comprises a 1,3,5-substituted phenyl moiety.

In a preferred embodiment of the cyclometallated complex of the present invention A comprises a triazole group substituted with an electron donating group, preferably an alkyl or alkylamine group, B comprises a phenyl group substituted with at least one fluorine or fluorinated group and said d-block transition metal is iridium. Most preferably said alkyl substituted triazole comprises a 1,2,4-triazole.

In all embodiments of the invention the group M is a d-block transition metal. M is preferably selected from iridium, rhodium, palladium, platinum, gold, osmium and ruthenium. Cyclometallated complexes of these metals have been shown to provide phosphorescent systems for use in organic electroluminescent devices. More preferably M is selected from iridium and platinum, both of which have been shown to provide high efficiency phosphorescent systems.

In an alternative embodiment the present invention provides a polymer or oligomer comprising a cyclometallated complex according to the present invention. Said cyclometallated complex may be incorporated into the main chain of the polymer or oligomer or said cyclometallated complex may be pendant to the main chain of the polymer or oligomer. Preferably said polymer or oligomer further comprises carbazole or triarylamine groups.

Further aspects and preferred features of the invention will now be considered with regard to specific compounds.

Compounds A-1 to A-7 below are examples of ligands where ring A is a five-membered ring and ring B is a phenyl ring. R represents a substituent, for example, hydrogen, an alkyl or aryl group or a halogen.

A-1
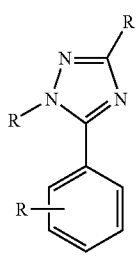

A-2
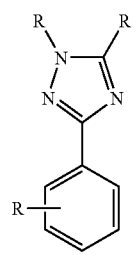

A-3
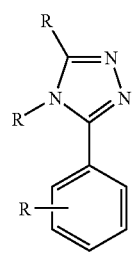

A-4
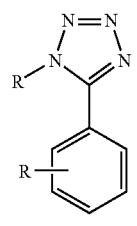

A-5
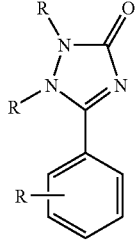

-continued

A-6
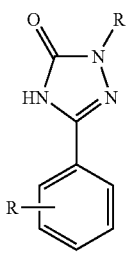

A-7
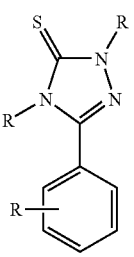

Ring A may be substituted, where ring A comprises a nitrogen this may also be substituted. Suitable substituents include alkyl and aryl groups, alkyloxy groups, alkylamines, arylamines, particularly diarylamines or triarylamines, carbazoles and halogen atoms, in particular fluorine or bromine. Electron donating groups are particularly suitable class of substituents and include alkoxy groups, alkyl groups, alkylamines and arylamines. Compounds B-1 to B-12 are examples of ligands with substituents on ring A.

B-1
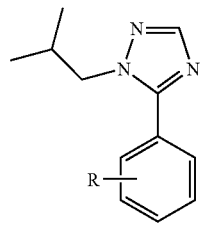

B-2
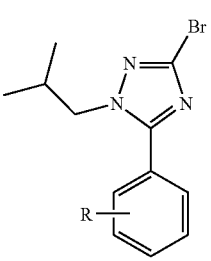

B-3
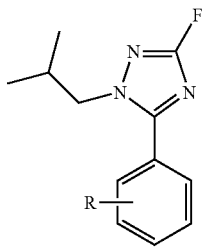

B-4 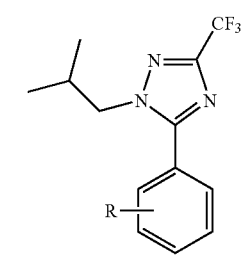

B-5 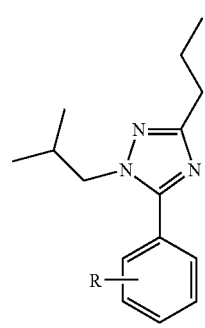

B-6 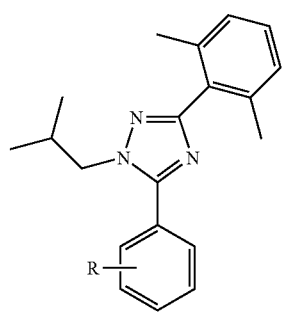

B-7 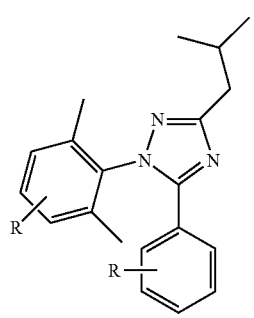

B-8 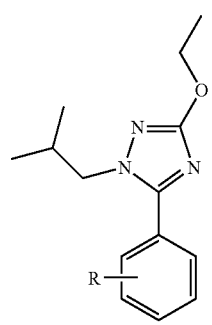

B-9 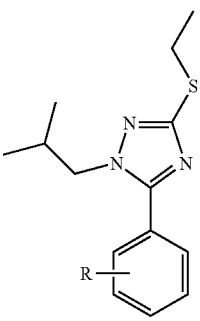

B-10 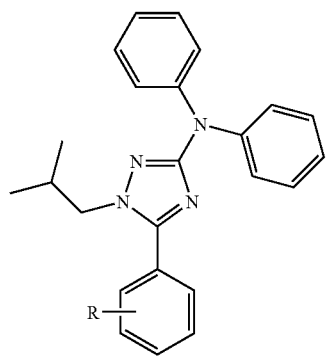

B-11 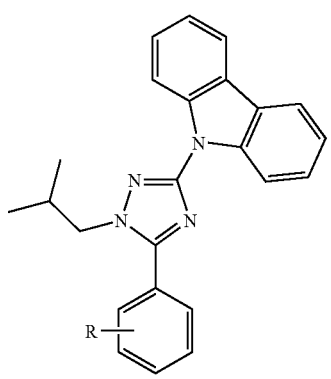

B-12

Alternatively ring A may be a six-membered heteroaromatic system, such as a triazine. Where ring A is a six-membered system it may be substituted with alkyl or aryl groups, halides or electron-donating groups. Compounds C-1 to C-3 show examples of suitable ligands wherein ring A is a six-membered ring. R represents a substituent, for example, hydrogen, an alkyl or aryl group or a halogen.

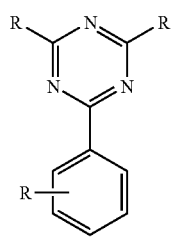

C-1

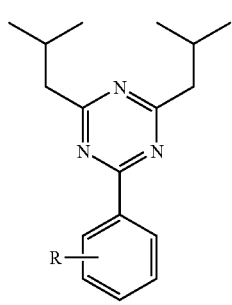

C-2

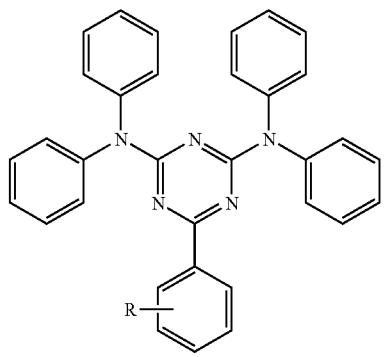

C-3

Ring B may be a five or six-membered ring and may be an aromatic or heteroaromatic ring such as benzene, pyridine, pyrazine, pyrimidine, thiophene, furan and pyrrole and derivatives of such groups. Ring B may be substituted or fused. Compounds D-1 to D-11 show suitable ligands wherein ring A is a triazole, clearly many other heteroaryl groups such as those described above may be selected for ring A. R represents a substituent, for example, hydrogen, an alkyl or aryl group or a halogen.

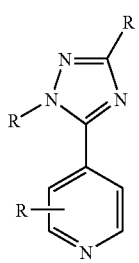

D-1

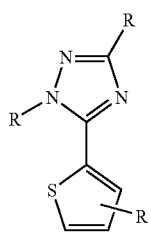

D-2

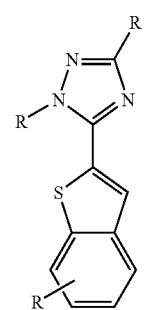

D-3

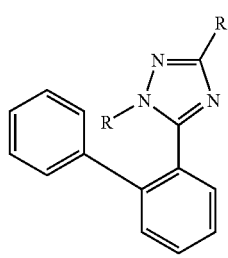

D-4

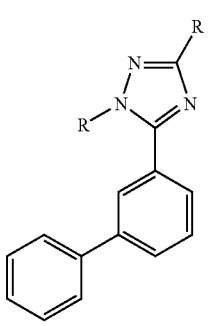

D-5

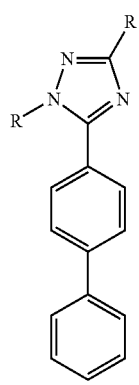

D-6

D-7 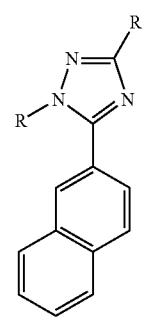

D-8 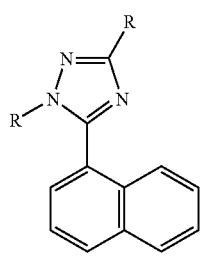

D-9 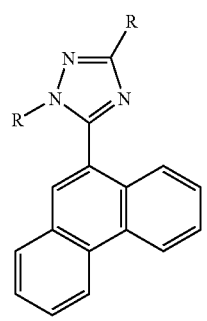

D-10 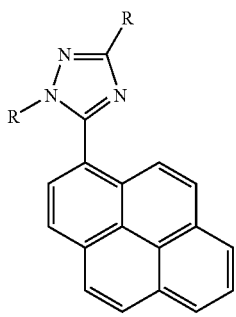

D-11 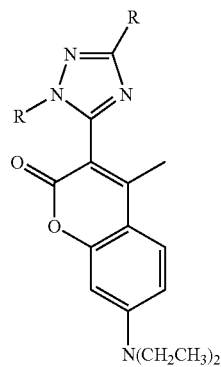

Rings A and B may be fused or linked by covalent bonds as shown in E-1 to E-4 below. R represents a substituent, for example, hydrogen, an alkyl or aryl group or a halogen.

E-1 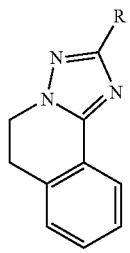

E-2 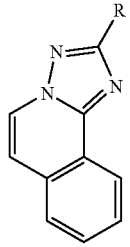

E-3 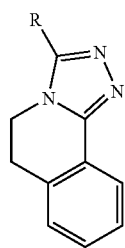

E-4 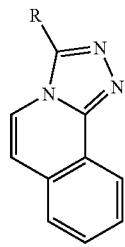

It is preferred that ring B is substituted with electron withdrawing groups such as fluorine, fluoroalkyl, fluoroalkoxy, sulfoxide or sulphone groups. Compounds F-1 to F-23 are examples of ligands substituted with electron withdrawing groups. R represents a substituent, for example, hydrogen, an alkyl or aryl group or a halogen.

F-1 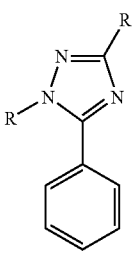

-continued
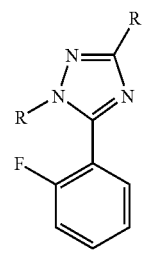  F-2
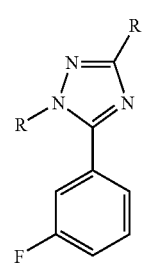  F-3
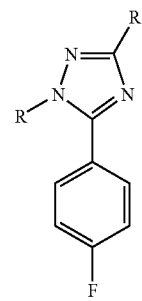  F-4
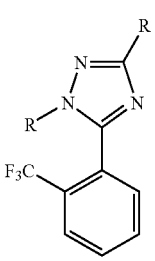  F-5
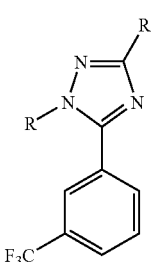  F-6
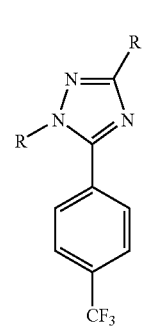  F-7
-continued
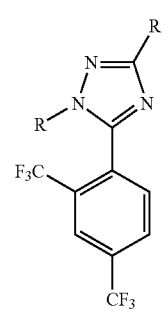  F-8
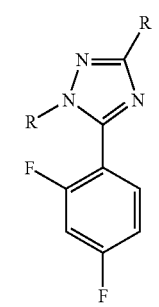  F-9
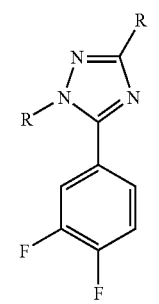  F-10
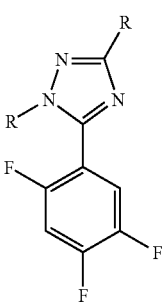  F-11
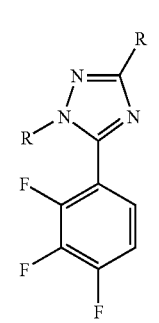  F-12

F-13 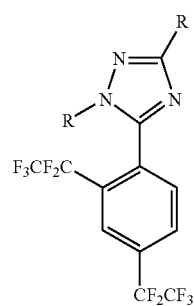
F-14 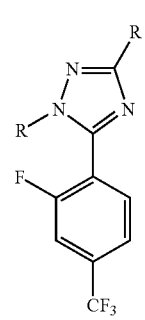
F-15 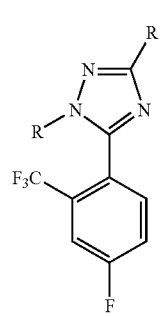
F-16 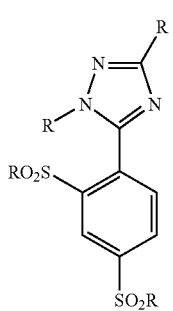
F-17 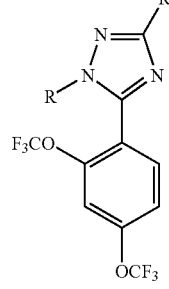
F-18 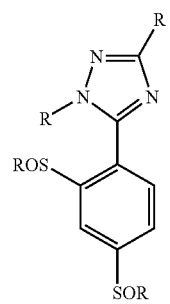
F-19 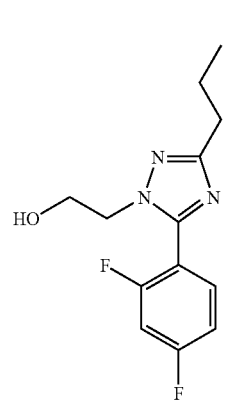
F-20 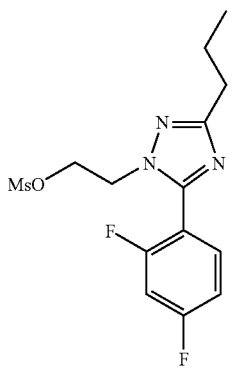
F-21 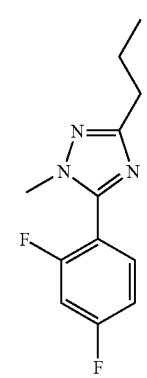

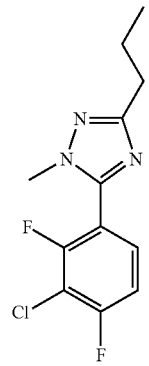

F-22

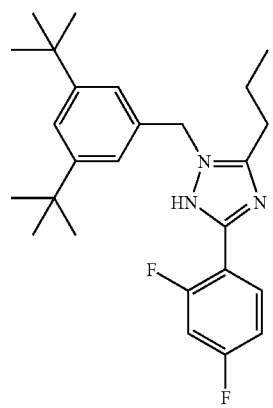

F-23

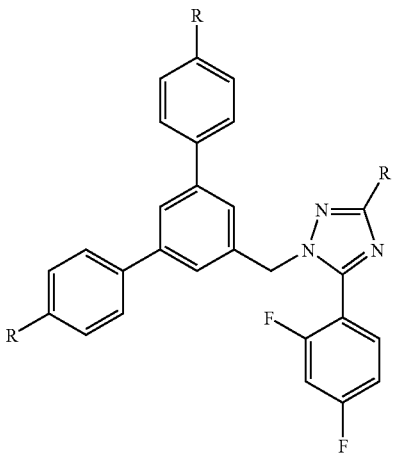

G-1

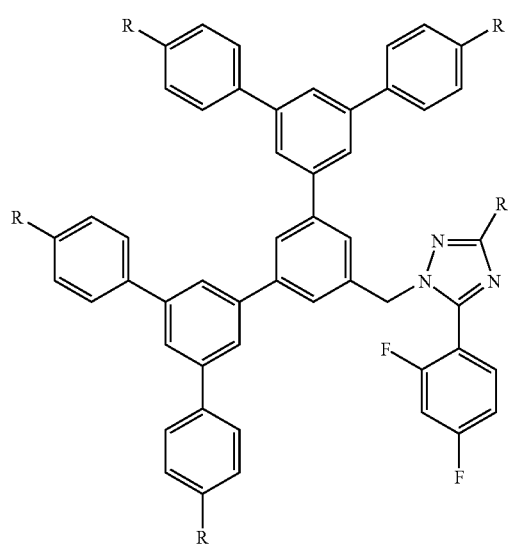

G-2

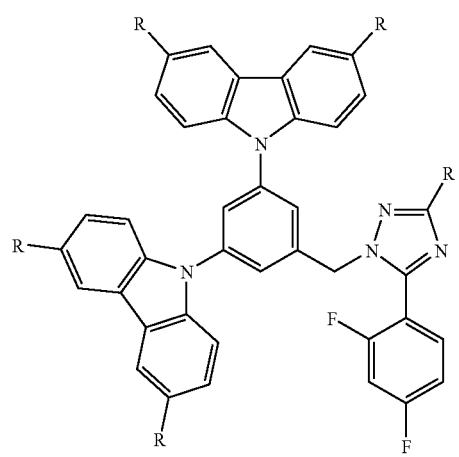

G-3

The ligand on metal M may be substituted with dendrons to provide enhanced solution processing properties and to introduce further functionality into the ligand, such as charge transporting functionality. Dendrons are branching structures which allow a high density of functionality to be introduced into the eventual metal complex. In the cyclometallated complexes of the present invention the central metal ion and the ligands forming the first coordination sphere will form the core of the dendrimer with the dendrons substituted onto ring A, B or both. It is preferred that the dendrons are substituted onto ring A of the ligand and that the dendrons are not conjugated to ring A. It has been found particularly advantageous to provide an alkylene linking group between the dendron and ring A, in particular a methylene or ethylene linking group. It is preferred that where ring B has dendron substituents these are in the para position to the carbon of ring B which will form a carbon-metal bond in the cyclometallated complex. Dendrons comprising carbazole, triarylamine and 1,3,5-phenyl groups are particularly suitable for application in light emitting devices. Compounds G-1 to G-9 show ligands according to the present invention substituted with dendrons at ring A. R represents a substituent, for example, hydrogen, an alkyl or aryl group or a halogen or an alkyloxy group.

G-4
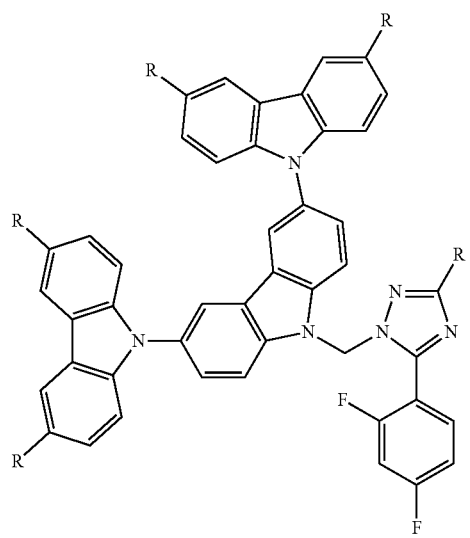
G-5
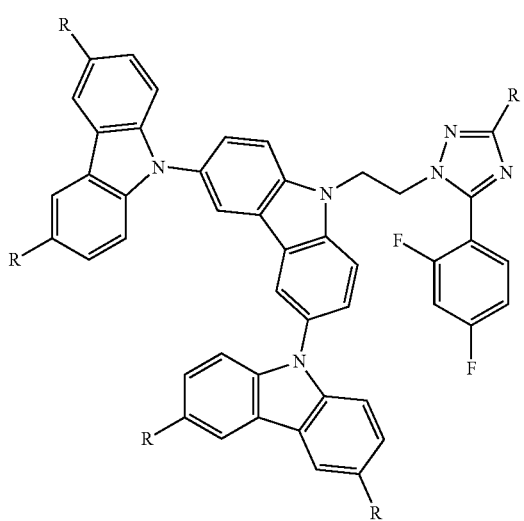
G-6
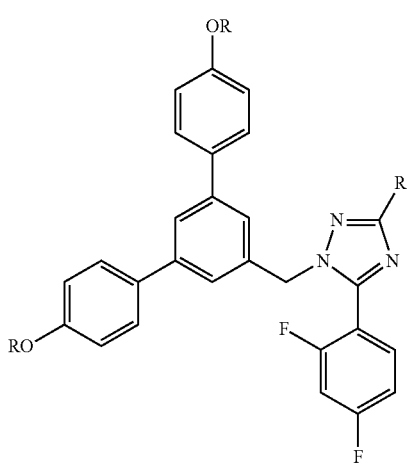
G-7
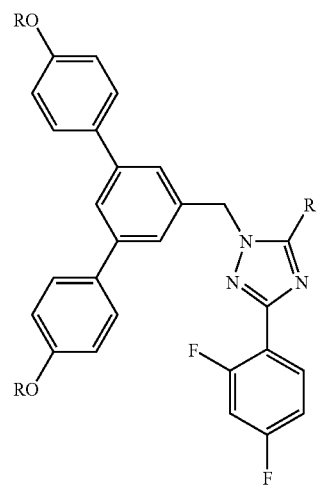
G-8
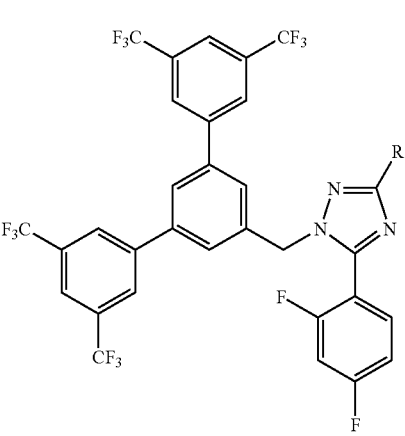
G-9
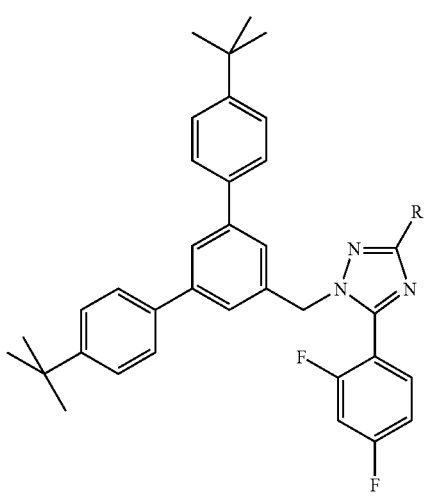
Ring A may also be substituted with a plurality of dendrons, for example, compounds H-1 and H-2 show ligands substituted with a pair of dendrons at ring A. R represents a substituent, for example, hydrogen, an alkyl or aryl group or a halogen.

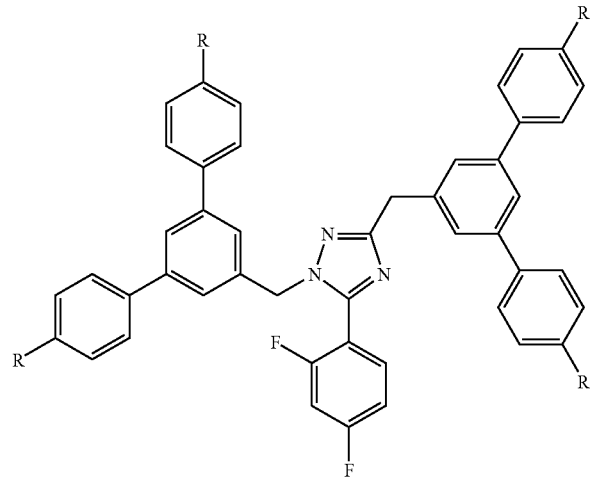
H-1
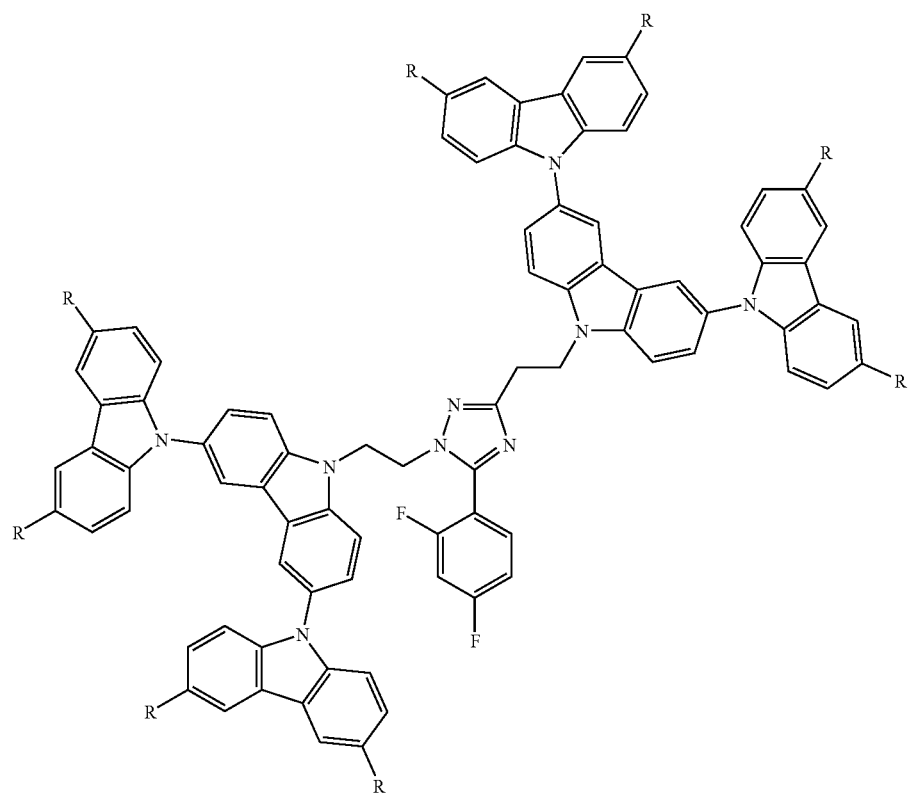
H-2

Ligands of the present invention may also be substituted at ring B with dendrons, as shown by compounds I-1 and I-2 below. R represents a substituent, for example, hydrogen, an alkyl or aryl group or a halogen.

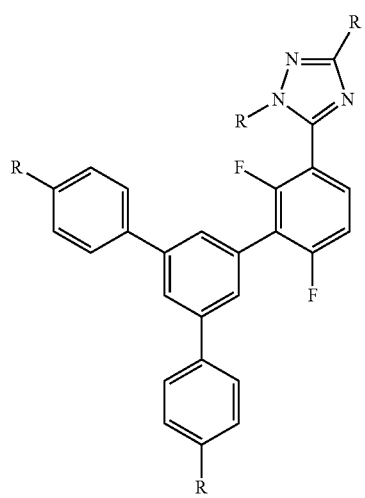

I-1

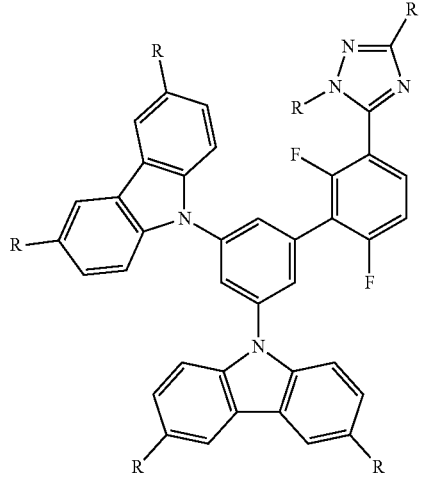

I-2

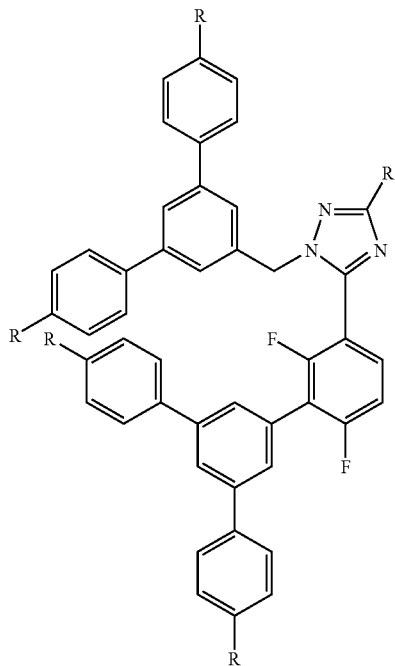

J-1

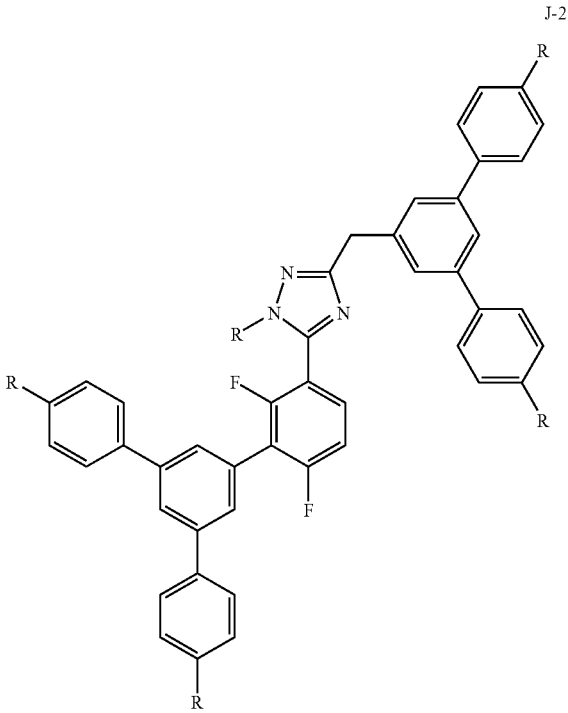

J-2

Alternatively both rings A and B may be substituted with dendrons, as shown by compounds J-1 to J-4 below. R represents a substituent, for example, hydrogen, an alkyl or aryl group or a halogen. United Kingdom patent application GB0219987.5 describes advantages associated with having a plurality of dendrons substituted around a metal core.

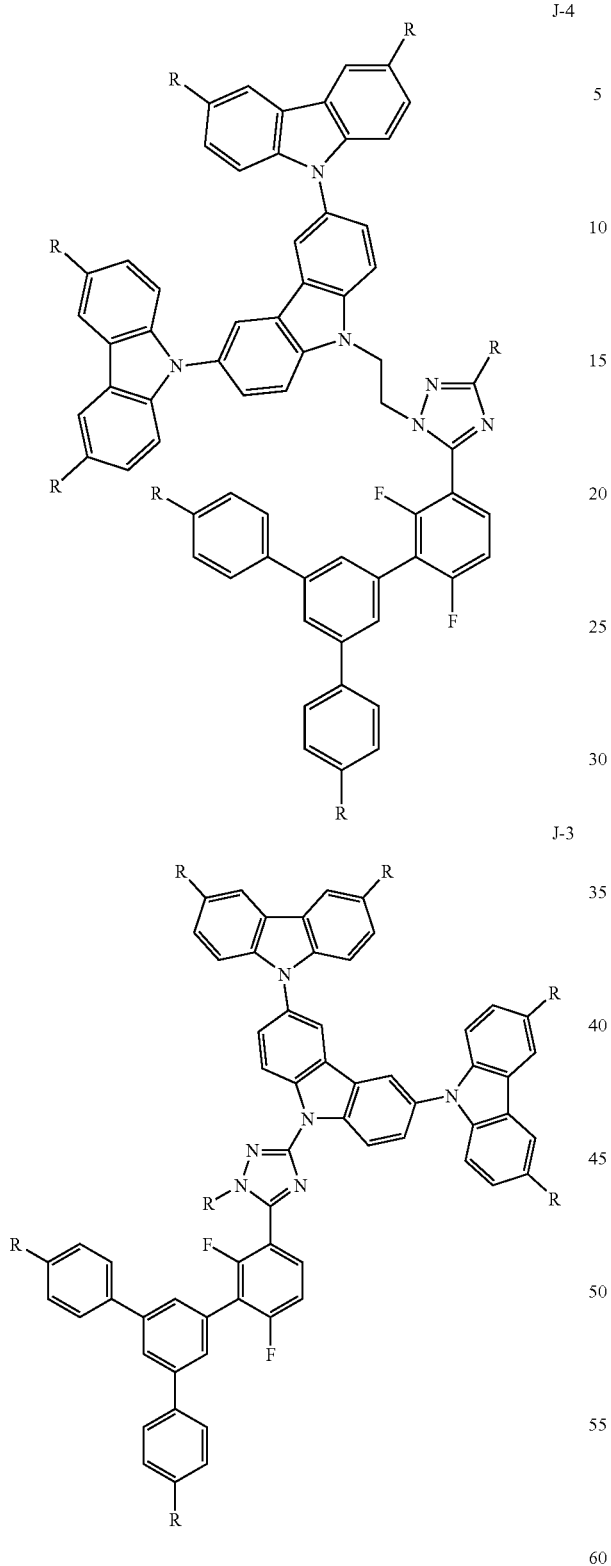

derivatives, carbonyl, nitrile, isonitrile and halides. Most preferably where said cyclometallated complex is heteroleptic it comprises a picolinate or a tetrakis(1-pyrazolyl)borate co-ligand. Where said cyclometallated complex is heteroleptic it may comprise a further ligand of the same general structure (i.e. having rings A and B linked in the same manner, and having ring A substituted n times by group $R_1$), but the definitions of A, B, $R_1$ and n may be different. Suitable homoleptic complexes include those compounds K-1 to K-5 below.

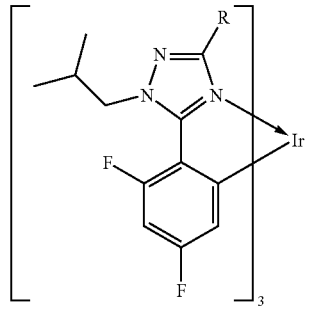

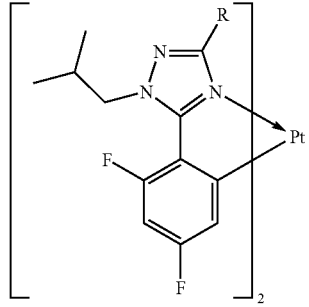

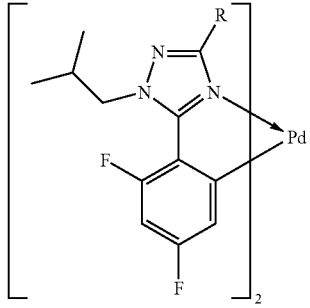

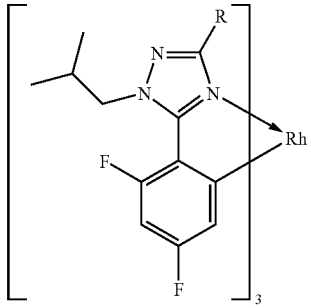

The cyclometallated complex of the present invention may be homoleptic or heteroleptic. In a homoleptic complex all ligands are identical, in a heteroleptic complex different ligands are bound to the metal.

Where said cyclometallated complex is heteroleptic it preferably comprises a ligand selected from the group comprising picolinates, acetylacetates, phosphines, pyridine and pyridine -continued

K-5

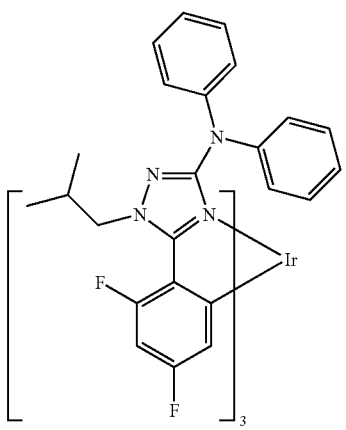

The cyclometallated complexes of the present invention may be heteroleptic complexes comprising different ligands of formula I, examples of such complexes are shown by compounds L-1 and L-2 below.

L-1

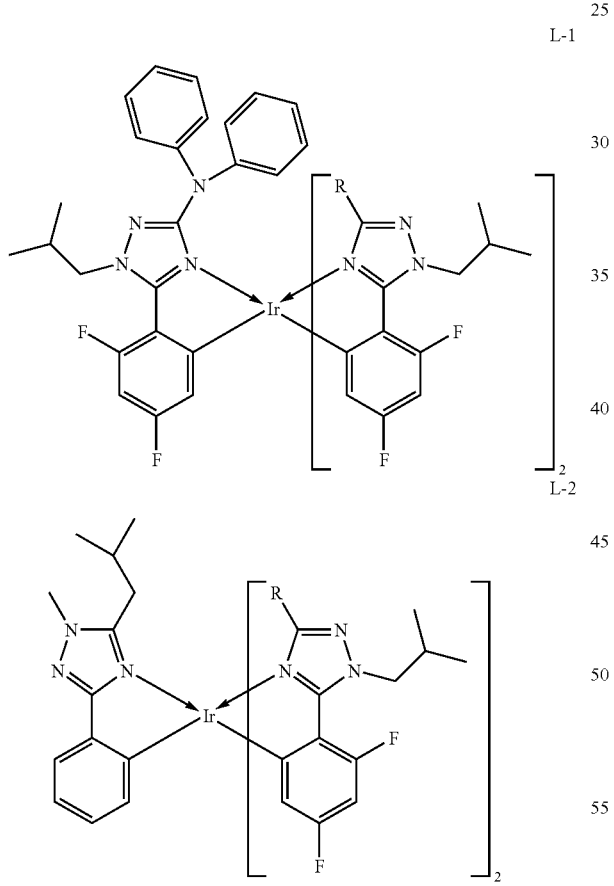

L-2

The cyclometallated complexes of the present invention may also be heteroleptic complexes comprising at least one ligand of formula I and other ligands of different structures. Examples of suitable ligands which may be used to form heteroleptic complexes in the present invention include phenylpyridines and other 2-substituted pyridines, 1,3-diones such as picolinates, phosphines and diphosphines and carboxylates. Picolinates are particularly preferred co-ligands. 1-Pyrazolylborates, such as tetrakis(1-pyrazolyl)borate are a preferred class of co-ligands. Compounds M-1 to M-15 are examples of suitable ligands for use in heteroleptic complexes according to the present invention.

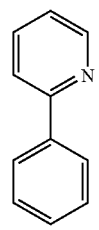

M-1

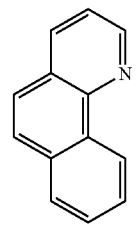

M-2

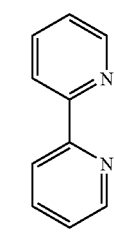

M-3

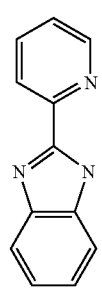

M-4

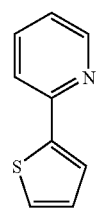

M-5

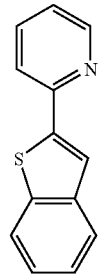

M-6

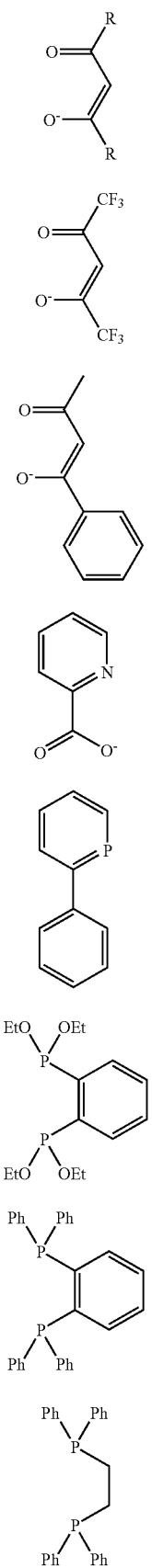

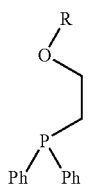

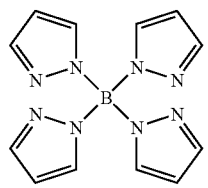

In addition to the bidentate co-ligands, examples of which are illustrated above, monodentate ligands may also be used as co-ligands in the cyclometallated complexes of the present invention. Examples of suitable monodentate ligands include carbonyl, nitrile, isonitrile and alkylisonitriles, thiocyanide, alkylphosphines and arylphosphines, in particular triphenylphosphine, halides, in particular chloride or bromide, heterocyclic compounds such as pyridine and substituted pyridines and alkynes. Preferred monodentate ligands include carbonyl, nitrile, isonitriles, triarylphosphines and halides.

Examples of heteroleptic complexes comprising ligands of formula I and ligands of different structures are shown by compounds N-1 to N-9 below. X represents a charged moiety with a charge sufficient to balance the charge of the metal complex and is preferably chloride, tetrafluoroborate or hexafluorophosphate.

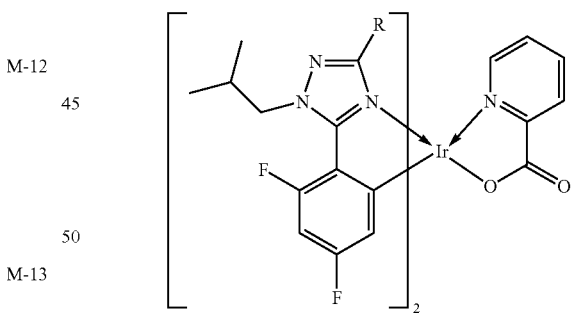

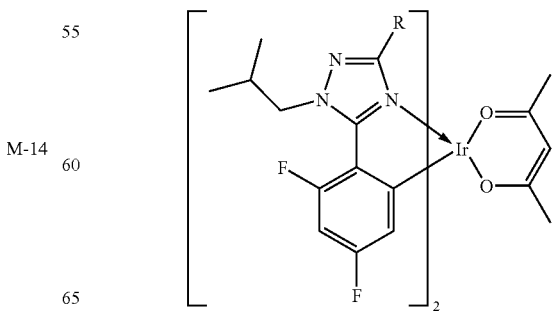

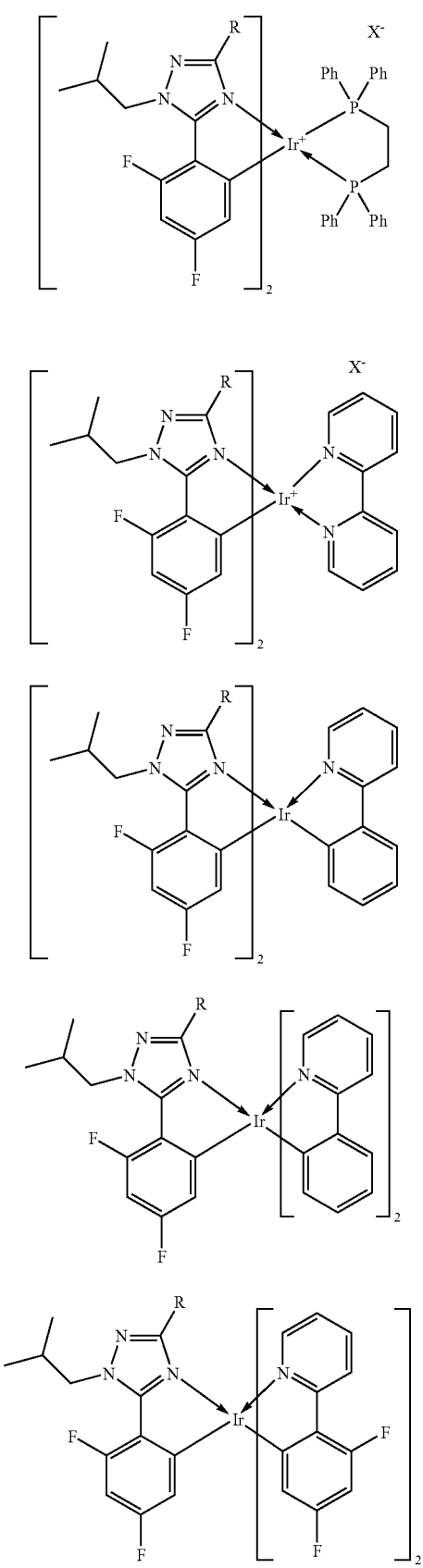

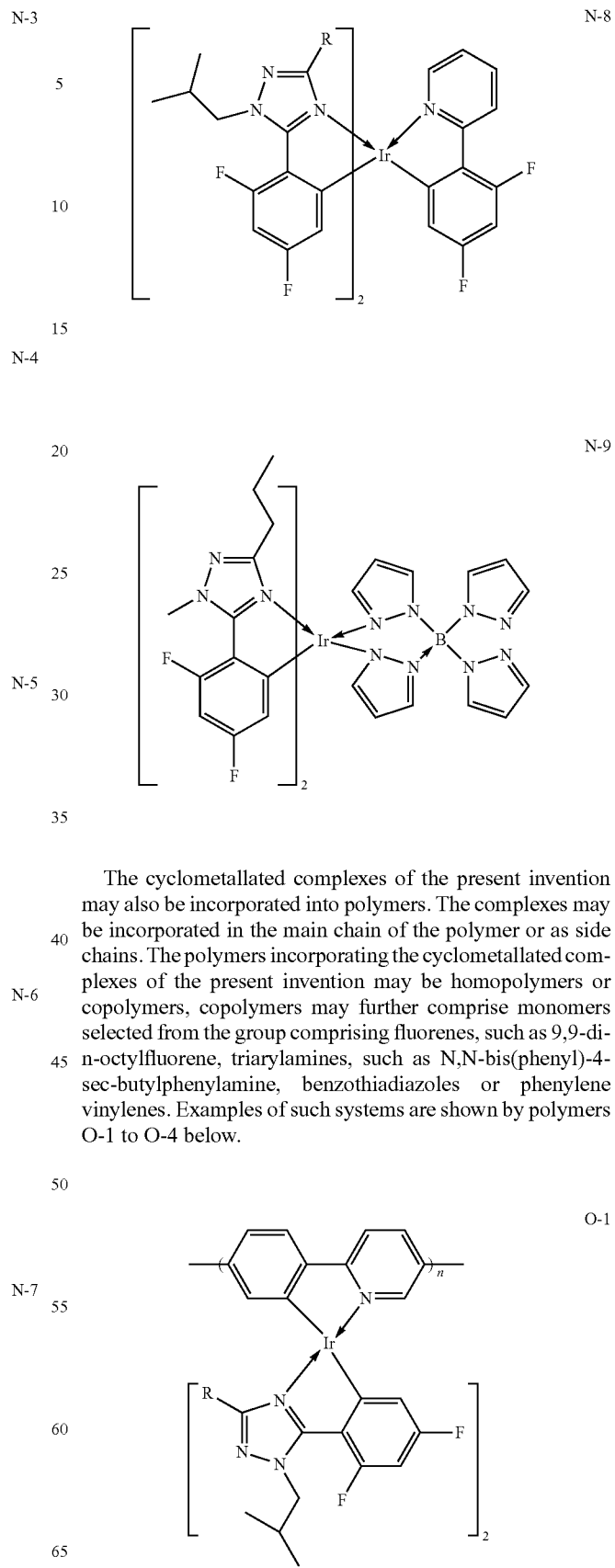

The cyclometallated complexes of the present invention may also be incorporated into polymers. The complexes may be incorporated in the main chain of the polymer or as side chains. The polymers incorporating the cyclometallated complexes of the present invention may be homopolymers or copolymers, copolymers may further comprise monomers selected from the group comprising fluorenes, such as 9,9-di-n-octylfluorene, triarylamines, such as N,N-bis(phenyl)-4-sec-butylphenylamine, benzothiadiazoles or phenylene vinylenes. Examples of such systems are shown by polymers O-1 to O-4 below.

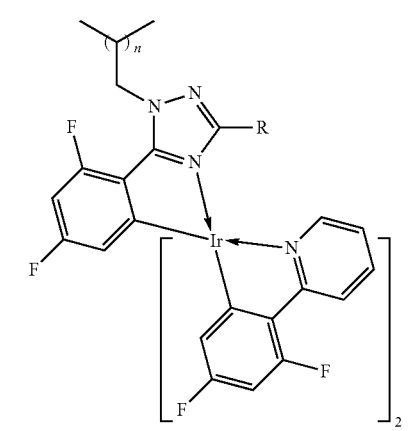

O-2

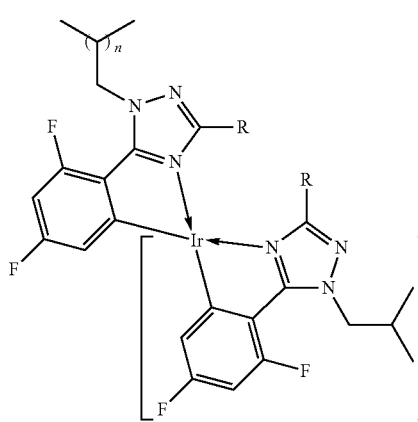

O-3

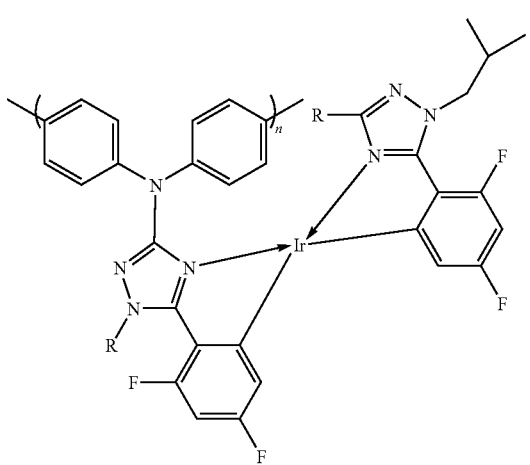

O-4

A particularly advantageous class of copolymers includes those copolymers which comprise the cyclometallated complexes of the present invention and a comonomer suitable to act as a host material such as carbazole, carbazole derivatives and triarylamines.

In an alternative embodiment of the invention there is provided a cyclometallated complex comprising the structure of formula II wherein A is a five- or six-membered heteroaryl ring which comprises at least three heteroatoms and which is optionally fused to another ring, B is a five- or six-membered aryl or heteroaryl ring which is optionally substituted and is optionally fused to another ring, n is greater than one and $R_1$ is a dendron or a solubilising group. The heteroatoms in ring A are preferably selected from oxygen, sulphur and nitrogen. More preferably ring A contains at least two nitrogen atoms, more preferably at least three nitrogen atoms. Preferably ring A contains 3, 4 or 5 heteroatoms, more preferably 3 or 4 heteroatoms. The preferred rings for A and B of this embodiment, the preferred $R_1$ substituents and the preferred values of n are as defined above in relation to the first embodiment of the invention.

Preferred dendrons are as described above in relation to the first embodiment of the invention defined with reference to formula I. Preferred solubilising groups include alkyl groups having 3 to 12 carbon atoms and heteroalkyl groups such alkoxy groups. Suitable alkoxy groups include $C_{1-6}$ alkoxy groups.

In a further embodiment of the invention there is provided a polymer comprising a cyclometallated complex comprising the structure of formula III wherein A is a five- or six-membered heteroaryl ring which comprises at least three heteroatoms and which is fused to another ring, B is a five- or six-membered aryl or heteroaryl ring which is optionally substituted and optionally fused to another aryl or heteroaryl ring, n is zero or greater than one and $R_1$ is a substituent other than hydrogen. The heteroatoms in ring A are preferably selected from oxygen, sulphur and nitrogen. More preferably ring A contains at least two nitrogen atoms, more preferably at least three nitrogen atoms. Preferably ring A contains 3, 4 or 5 heteroatoms, more preferably 3 or 4 heteroatoms.

The preferred rings for A and B of this embodiment, the preferred $R_1$ substituents and the preferred values of n are as defined above in relation to the first embodiment of the invention.

The inventors of the present invention have surprisingly found that a class of cyclometallated iridium complexes of formula I emit light having a blue colour. Cyclometallated iridium complexes of formula I wherein ring A is a five membered ring and is substituted with an electron donating group and wherein ring B is a phenyl ring and is substituted with at least one electron withdrawing group have been shown to emit blue light. In particular cyclometallated iridium complexes of formula I wherein ring A comprises a triazole substituted with an alkyl group and ring B comprises a phenyl ring substituted meta to the carbon-metal bond with two electron withdrawing groups selected from fluorine and trifluoromethane have been shown to emit light of a deep blue colour. Preferably the complexes of the invention have a CIE-y coordinate of less than 0.30, preferably less than 0.25, more preferably between 0.15 and 0.25.

For the purposes of the present invention blue light is considered to comprise light having CIE (Commission Internationale de l'Eclairage) coordinates of $0.3 > x > 0.05$ and $0.3 > y > 0.01$ and a wavelength of between 430 and 490 nm and deep blue is considered to comprise light having CIE coordinates of $0.3 > x > 0.1$ and $0.2 > y > 0.01$ and a wavelength of between 430 and 470 nm. The CIE defines the primary colour blue to have a wavelength of 435.8 nm and the PAL television system uses a blue light source with CIE coordinates of $x=0.15$, $y=0.06$.

The prior art blue phosphorescent light emitting iridium complexes of which Firpic referred to above is an example emit light of a light blue colour having CIE coordinates of $x=0.16$, $y=0.29$ with maximum emission at a wavelength of 470 nm.

The cyclometallated complex P-1, shown below, has the photoluminescent spectrum, shown in FIG. 1, having a peak emission at a wavelength of 450 nm with additional peaks at 428 and 490 nm and CIE coordinates of $x=0.15$, $y=0.09$. Clearly the photoluminescence of this cyclometallated complex is significantly blue shifted in comparison with the prior art blue phosphorescent emitter Firpic. The CIE coordinates of the complex are a deeper blue than the prior art blue phosphorescent systems and as such are more suitable for producing full colour displays. The dendron substituted complex P-3 shows CIE coordinates of x=0.16, y=0.14.

picolinates, acetylacetates, tetrakis(1-pyrazolyl)borate and nitrile. Examples of cyclometallated iridium complexes incorporating both the above described ligands and blue shifting coligands are shown below, compounds Q-1 to Q-2.

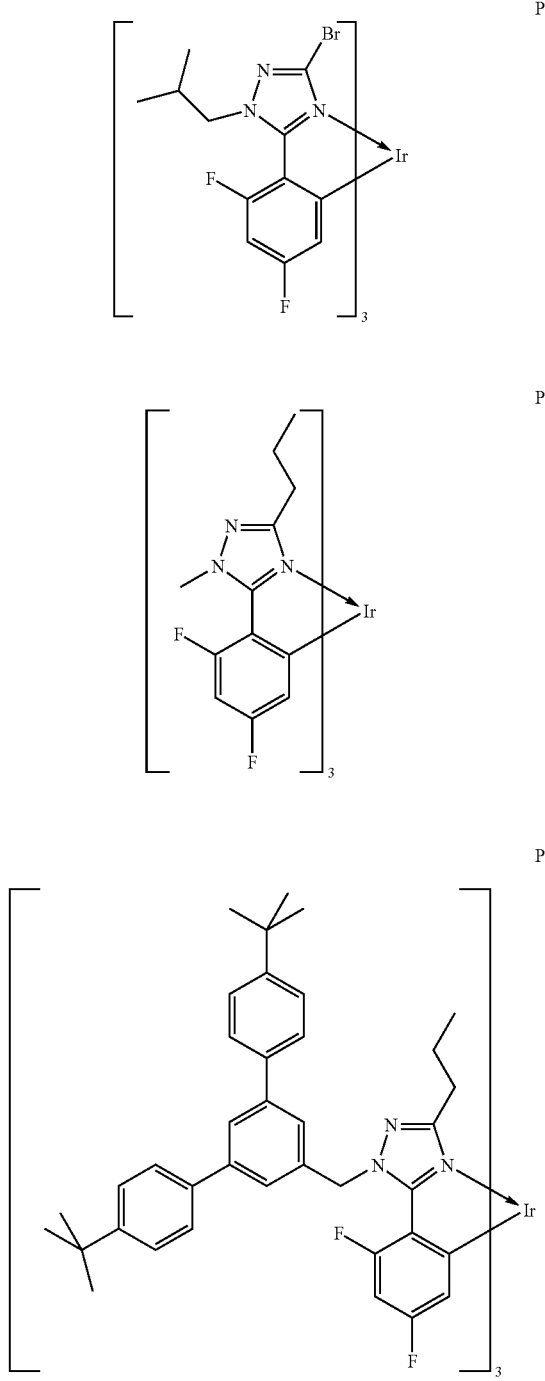

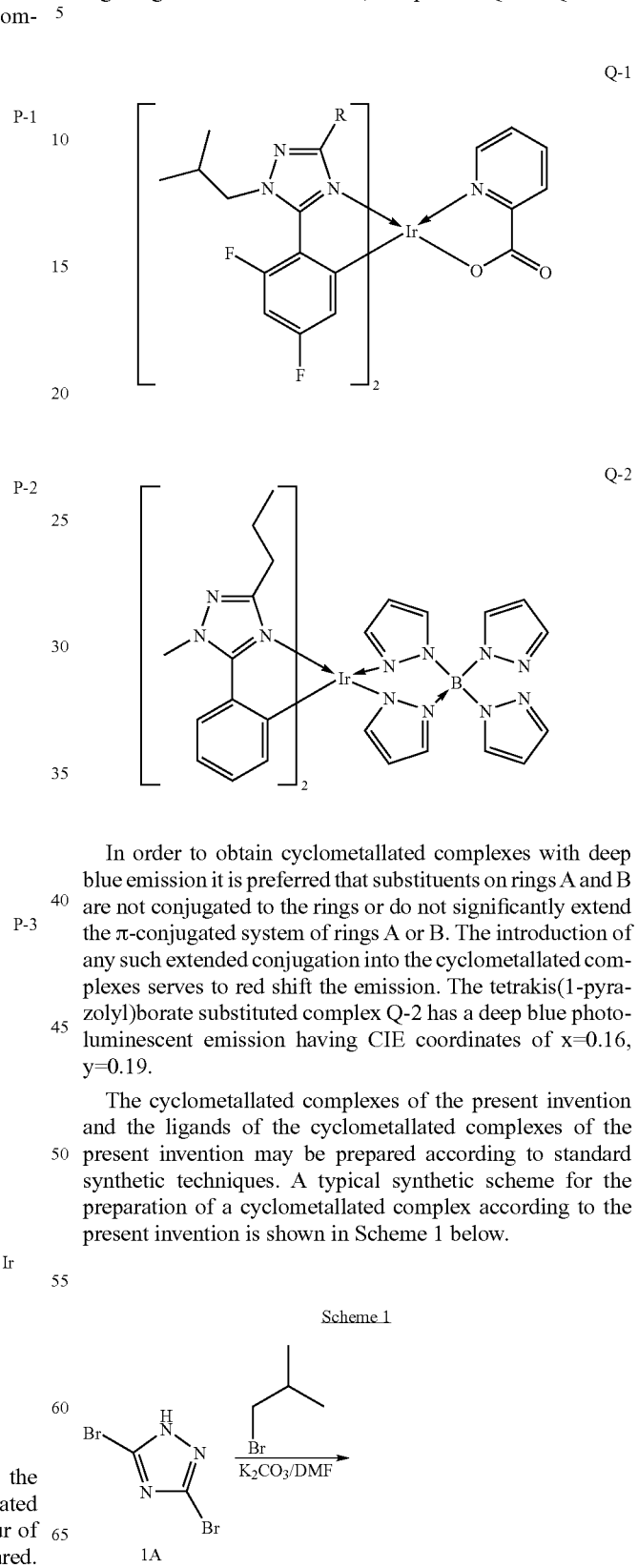

In order to obtain cyclometallated complexes with deep blue emission it is preferred that substituents on rings A and B are not conjugated to the rings or do not significantly extend the π-conjugated system of rings A or B. The introduction of any such extended conjugation into the cyclometallated complexes serves to red shift the emission. The tetrakis(1-pyrazolyl)borate substituted complex Q-2 has a deep blue photoluminescent emission having CIE coordinates of x=0.16, y=0.19.

The cyclometallated complexes of the present invention and the ligands of the cyclometallated complexes of the present invention may be prepared according to standard synthetic techniques. A typical synthetic scheme for the preparation of a cyclometallated complex according to the present invention is shown in Scheme 1 below.

Heteroleptic complexes comprising ligands used in the above-described blue light emitting iridium cyclometallated complexes and further ligands known to shift the colour of light emission of the complexes may also be prepared. Examples of such ligands include anionic ligands such as

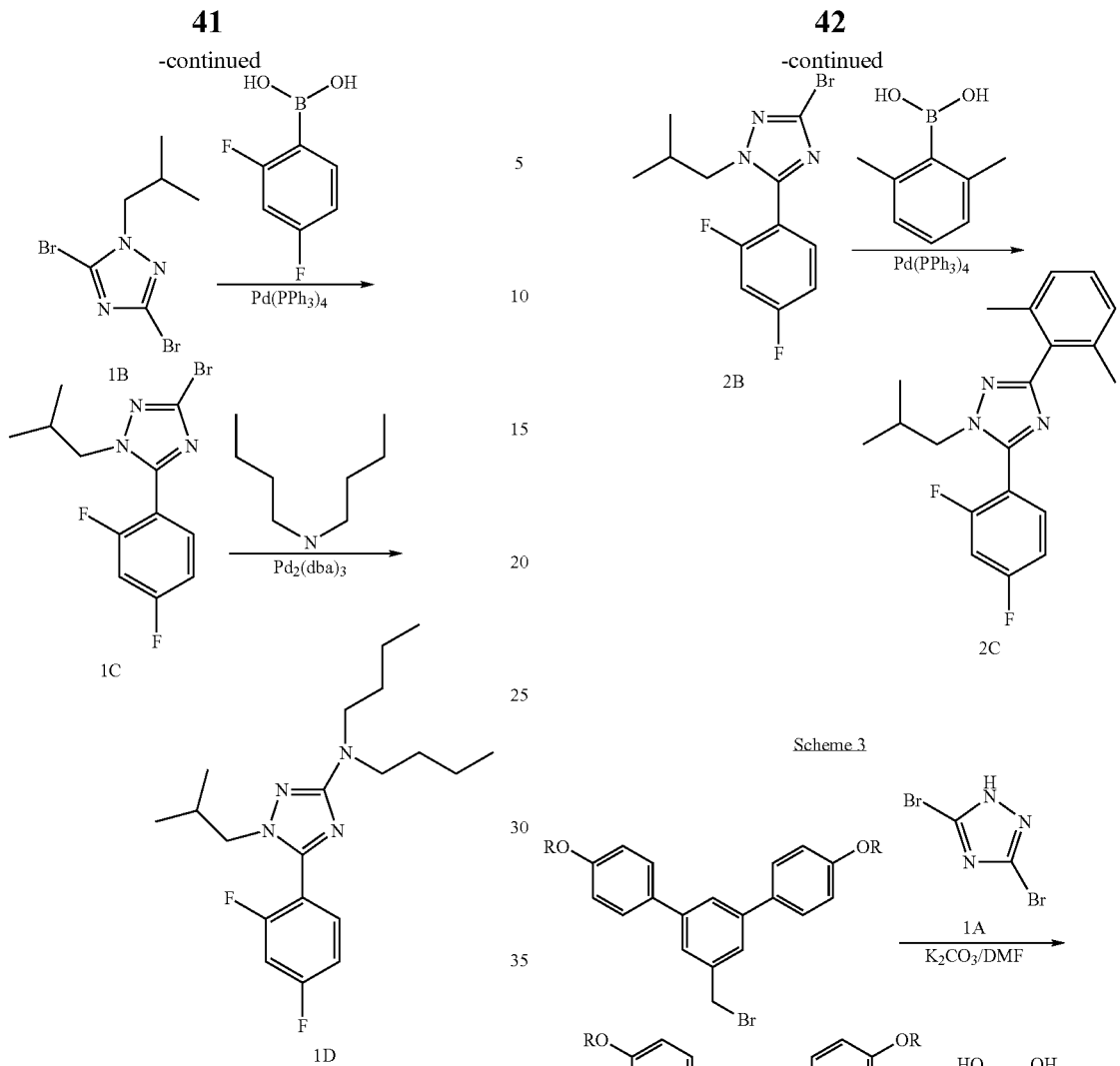

In the above Scheme 1 a dibrominated triazole 1A is reacted with excess iso-butylbromide in the presence of a base to provide the substituted triazole 1B. The substituted triazole 1B is further reacted with a phenyl substituted boronic acid using Suzuki coupling to provide compound 1C. Compound 1C is then further substituted with dipropylamine in the presence of tris(dibenzylideneacetone)dipalladium(0) ((Pd₂(dba)₃)) to provide the ligand 1D. This synthetic methodology allows a wide range of ligands to be prepared. The flexibility of the synthetic methodology is highlighted by synthetic schemes 2 and 3 shown below for the preparation of a range of ligands including dendron substituted ligands.

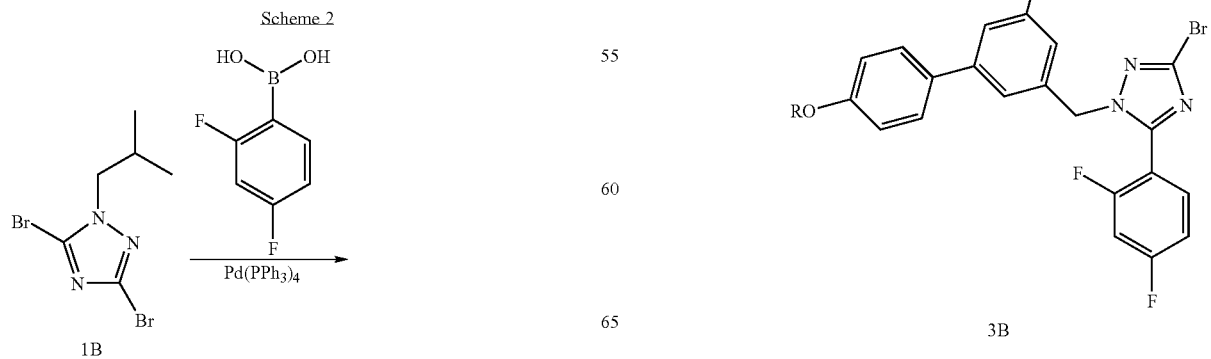

Metal complexes of the ligands can be prepared by standard synthetic techniques, in particular as described in Inorganic Chemistry (1994), 33(3), 545-50. In the procedure shown in Scheme 4 below excess phenyltriazole ligand 1C is reacted with iridium chloride in a protic solvent. The dimer complex 4A is isolated from the reaction mixture and reacted with further phenyltriazole ligand 1C in the presence of silver trifluoromethane sulfonate to give cyclometallated iridium complex 4B. Alternatively the dimer complex 4A may be reacted with a different co-ligand to give a heteroleptic complex such as 4C.

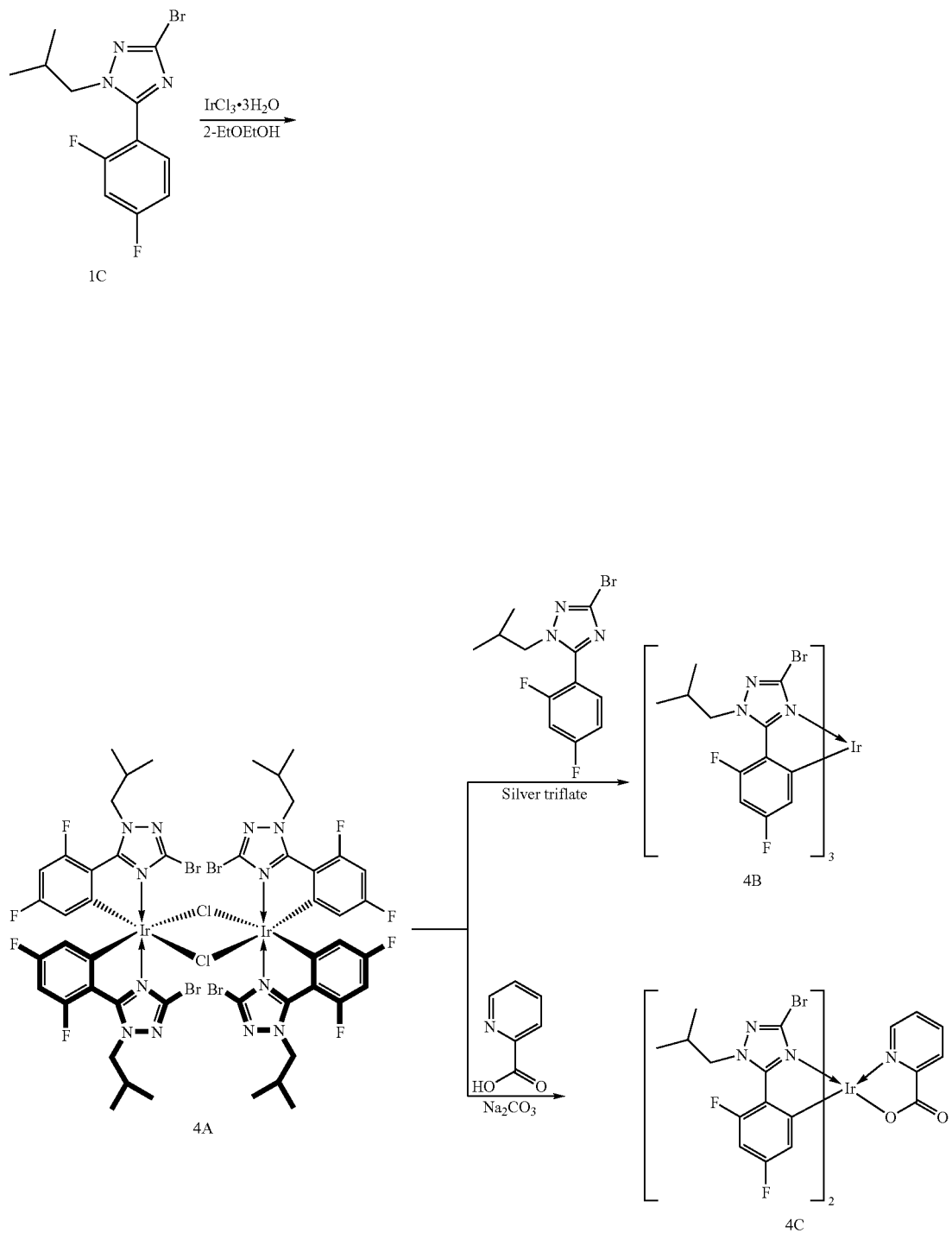

Scheme 5 shows an alternative and more preferred approach to the preparation of triazole based ligands comprising a triazole ring.
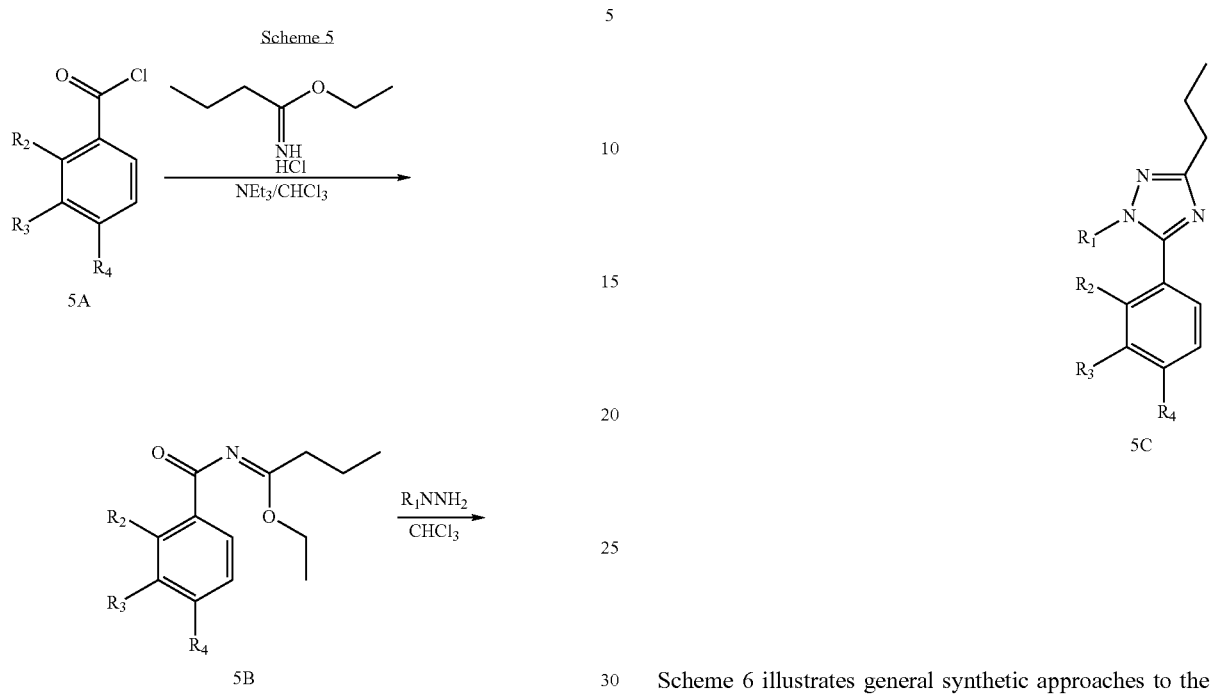
Scheme 6 illustrates general synthetic approaches to the cyclometallated iridium complex 6B to 6D.
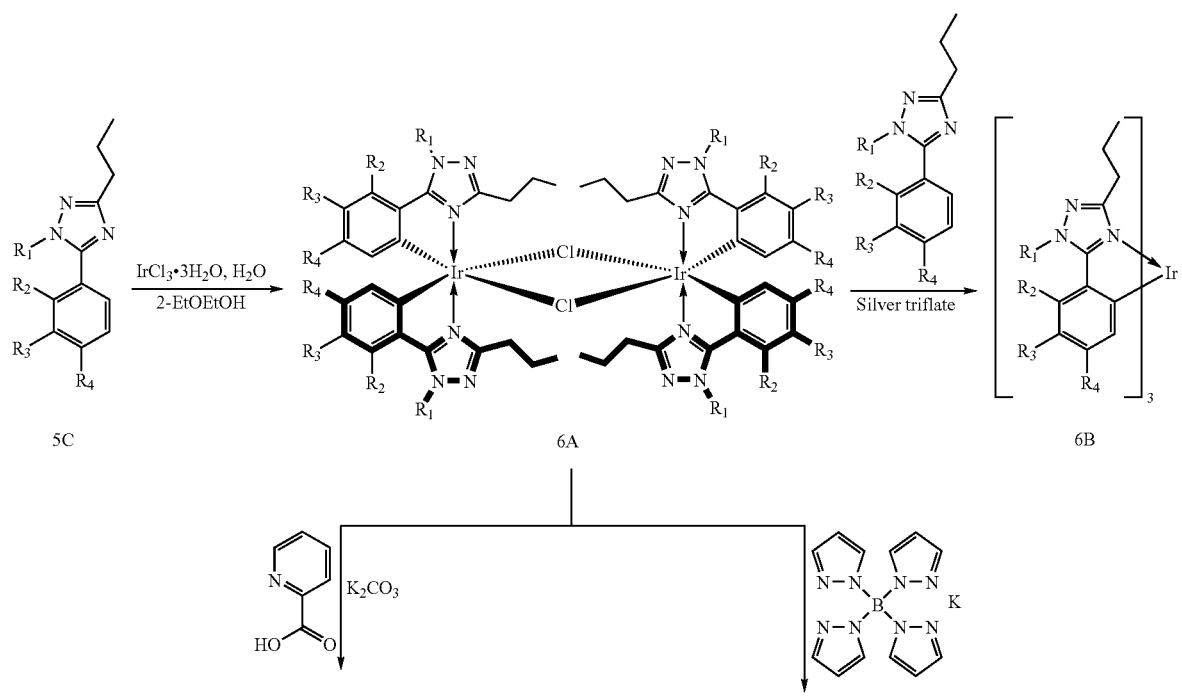

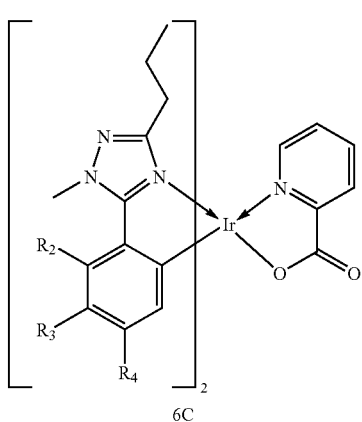

6C

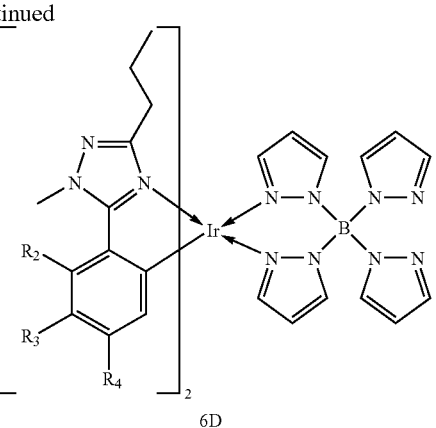

6D

Where the cyclometallated complexes of the present invention comprise dendrons these may be substituted onto the ligand prior to complexation of the ligand with the metal or alternatively the cyclometallated core may be formed first and the dendrons substituted onto the cyclometallated core.

The cyclometallated complexes of the present invention have application in organic optoelectronic devices. Organic optoelectronic devices include electroluminescent, photoluminescent, fluorescent and photoconductive organic devices and organic transistors. Photoconductive organic devices include photovoltaic devices, photodiodes and photosensors. In particular the cyclometallated complexes of the present invention have application in organic light emitting diodes.

Organic light emitting diodes comprise a layered structure comprising a lower electrode situated on a substrate, a layer, or several layers, of organic light emitting material and an upper electrode. When a voltage is supplied across the electrode of the device opposite charge carriers, namely electrons and holes, are injected into the organic light emitting material. The electrons and holes recombine in the layer of organic light emitting material forming an excited state (or exciton) which can decay radiatively (with the emission of light) or non-radiatively. In the case of fluorescent organic light emitters the radiative excited states are singlet excitons, in the case of phosphorescent organic light emitters the radiative excited states are triplet excitons. The cyclometallated complexes of the present invention are phosphorescent organic light emitters and in particular the cyclometallated complexes of the present invention comprising iridium and platinum form highly efficient phosphorescent light emitters.

The organic light emitting layer of organic phosphorescent light emitting devices generally comprises an organic phosphorescent light emitter, such as the cyclometallated complexes of the present invention, and an organic host. The organic host acts to transport charge to the phosphorescent emitter and also acts as a triplet source whereby triplet excited states are formed in the organic host and then transferred to the phosphorescent emitter where they decay with the emission of light. Prior art organic hosts used in phosphorescent light emitting systems include carbazoles such as polyvinylcarbazole, known as PVK, 4,4'-bis(carbazol-9-yl)biphenyl), known as CBP, N,N-dicarbazolyl-3,5-benzene, known as mCP, diphenyldi(o-tolyl) silane or p-bis(triphenylsilyly)benzene, known as UGH1 and UGH2 respectively and described in Holmes et al. (*Appl. Phys. Lett.,* 83, no. 18, 2003, 3818), and (4,4',4"-tris(carbazol-9-yl)triphenylamine), known as TCTA, such hosts are described in Ikai et al. (*Appl. Phys.* *Lett.,* 79 no. 2, 2001, 156). One particularly suitable host material is di(tert-butyl)CBP, which has the structure:

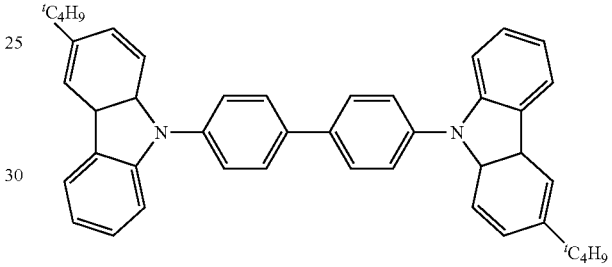

Triarylamines may also be used as host materials, in particular tris-4-(N-3-methylphenyl-N-phenyl)phenylamine, known as MTDATA. Where the phosphorescent emitter and the host are both soluble they may be deposited as a blend by solution processing techniques such as spin-coating, doctor blade coating, screen printing or ink-jet printing. Where the phosphorescent emitter and the host are insoluble and volatile they may be deposited by vacuum deposition. The phosphorescent emitter and host are preferably present in a blend comprising 5 to 50 mol % of phosphorescent emitter, preferably 10-30 mol % of phosphorescent emitter. Tetraarylsilane hosts are preferred, the tetraarylsilanes UGH1 and UGH2 are particularly preferred. Wide band gap hosts, such as tetraarylsilanes, are particularly preferred as hosts for cyclometallated complexes of the present invention which emit blue light.

Organic phosphorescent light emitting devices comprising a separate light emitter and host are well known in the prior art. More recently it has been found advantageous to combine the phosphorescent light emitter and the organic host in a single molecule, dendrimer or polymer, examples of such systems are disclosed in GB0206356.8. Advantages of such systems include improved film stability (no phase separation), improved electrochemical stability, improved manufacturability of devices, in particular improved solution processing properties, and improved light emission. As discussed above, in the cyclometallated complexes of the present invention host moieties can be introduced as substituents directly onto the aryl or heteroaryl rings A and/or B, by incorporation of the host moieties into dendrons attached to rings A and/or B or by forming copolymers comprising monomers of the cyclometallated complexes of the present invention and comonomers incorporating host moieties.

The organic light emitting layer of the light-emitting devices of the present invention may further comprise a diluent compound. In particular, polymethylmethacrylate (PMMA) may be admixed with the cyclometallated complex of the invention and the host material. This optional PMMA is used to dilute the concentration of host and dopant materials in the phosphorescent layer in order to prevent quenching effects which can occur at higher concentrations. Since PMMA is not a charge transporting material, the quantity used is a balance between minimising quenching and maintaining good conductivity in the phosphorescent layer. Preferred levels of PMMA in the phosphorescent layer are from 0 to 90% by weight, more preferably from 30 to 80%, more preferably 50 to 80%, most preferably 50 to 75%.

In addition to increasing quantum efficiency, PMMA may also contribute to improving film formation.

The light emitting organic layer preferably has a thickness of between 5 and 200 nm, more preferably of between 10 and 60 nm and most preferably of between 20 and 50 nm. The light emitting layer incorporating a phosphorescent emitter and a host may also include hole-transport materials examples of which are discussed below.

One of the electrodes of the organic light emitting device, the anode, comprises a high work function material suitable for injecting holes into the layer of organic light emitting material, this material typically has a work function of greater than 4.3 eV and may be selected from the group comprising indium-tin oxide (ITO), tin oxide, aluminum or indium doped zinc oxide, magnesium-indium oxide, cadmium tin-oxide, gold, silver, nickel, palladium and platinum. The anode material is deposited by sputtering or vapour deposition as appropriate. Incorporation of a thin layer of, for example, silicon oxide, over the surface of the anode, in particular over ITO, can improve the performance of organic light emitting devices, as shown in WO02/093662.

The other electrode, the cathode, comprises a low work function material suitable for injecting electrons into the layer of organic light emitting material. The low work function material typically has a work function of less than 3.5 eV and may be selected from the group including Li, Na, K, Rb, Be, Mg, Ca, Sr, Ba, Yb, Sm and Al. The cathode may comprise an alloy of such metals or an alloy of such metals in combination with other metals, for example the alloys MgAg and LiAl. The cathode preferably comprises multiple layers, for example Ca/Al, Ba/Al or LiAl/Al. The device may further comprise a layer of dielectric material between the cathode and the emitting layer, such as is disclosed in WO 97/42666. In particular it is preferred to use an alkali or alkaline earth metal fluoride as a dielectric layer between the cathode and the emitting material. A particularly preferred cathode comprises LiF/Al, with a layer of LiF of thickness from 1 to 10 nm and a layer of Al of thickness 10 to 500 nm. The cathode materials are deposited by vacuum deposition methods.

For light emission to occur from the device it is preferred that either the cathode, the anode or both be transparent or semi-transparent. Suitable materials for transparent anodes include ITO and thin layers of metals such as platinum. Suitable materials for transparent cathodes include a thin layer of electron injecting material in proximity to the layer of organic light emitting material and a thicker layer of transparent conductive material overlying the layer of electron injecting material e.g. a cathode structure comprising Ca/Au. Where neither the cathode nor the anode is transparent or semi-transparent light emission occurs through the edge of the device.

The organic light emitting device may include further organic layers between the anode and cathode to improve charge injection and device efficiency. In particular a layer of hole-transporting material may be situated over the anode. The hole-transport material serves to increase charge conduction through the device. The preferred hole-transport material used in the art is a conductive organic polymer such as polystyrene sulfonic acid doped polyethylene dioxythiophene (PEDOT:PSS) as disclosed in WO98/05187. Other hole transporting materials such as doped polyaniline, TPD (N,N'-diphenyl-N,N'-bis(3-methylphenyl)[1,1'-biphenyl]-4,4'-diamine), NPD (4,4'-bis[N-naphthyl)-N-phenyl-amino]biphenyl) and MTDATA may also be used. A hole transport layer which has been shown to be particularly advantageous when used in combination with cyclometallated complexes comprises polymerised divinyl-TPD.

The cyclometallated complexes of the present invention may comprise a hole transporting moiety. The advantages of incorporating the hole transporting function into the cyclometallated complex include improved film stability and improved manufacturability. The hole transporting groups may be incorporated into the cyclometallated complexes as substituents directly on the ligands, for example as dendrons, or by being present as comonomers in copolymers comprising the cyclometallated complexes of the present invention. The cyclometallated complexes of the present invention may also comprise an electron transporting moiety.

A layer of electron transporting/hole blocking material may be positioned between the layer of light emitting material and the cathode, this has been found to improve device efficiency. Suitable materials for electron transporting/hole blocking layers include 2,9-dimethyl-4,7-diphenyl-1,10-phenanthroline (BCP), 1,3,5-tris(2-N-phenylbenzimidazolyl)benzene (TPBI) and 2-biphenyl-5(4'-t-butylphenyl) oxadiazole (PBD). The provision of an electron transporting/hole blocking layer between the light emitting layer and the cathode has been found to significantly improve device performance both in terms of device efficiency and lifetime.

The substrate of the organic optoelectronic device should provide mechanical stability to the device and act as a barrier to seal the device from the environment. Where it is desired that light enter or leave the device through the substrate, the substrate should be transparent or semi-transparent. Glass is widely used as a substrate due to its excellent barrier properties and transparency. Other suitable substrates include ceramics, as disclosed in WO 02/23579 and plastics such as acrylic resins, polycarbonate resins, polyester resins, polyethylene terephthalate resins and cyclic olefin resins. Plastic substrates may require a barrier coating to ensure that they remain impermeable. The substrate may comprise a composite material such as the glass and plastic composite disclosed in EP 0 949 850.

To provide environmental protection the device is encapsulated. Encapsulation may take the form of a glass sheet which is glass bonded to the substrate with a low temperature frit material. To avoid the necessity of using a glass sheet to encapsulate the device a layer of passivating material may be deposited over the device. Suitable barrier layers comprise a layered structure of alternating polymer and ceramic films and may be deposited by PECVD as disclosed in WO 00/36665 and U.S. Pat. No. 5,686,360. Alternatively the device may be encapsulated by enclosure in a metal can.

Preferred device structures for the phosphorescent light emitting cyclometallated complexes of the present invention include:

Glass/ITO/PEDOT:PSS/CBP:emitter/TPBI/LiF/Al
Glass/ITO/poly(vinyl-TPD)/CBP:emitter/TPBI/LiF/Al Glass/ITO/SiO/PEDOT:PSS/CBP:emitter/TPBI/LiF/Al
Glass/ITO/SiO/poly(vinyl-TPD)/CBP:emitter/TPBI/LiF/Al
Glass/ITO/PEDOT:PSS/PVK:emitter/TPBI/LiF/Al.
Glass/ITO/poly(vinyl-TPD)/PVK:emitter/TPBI/LiF/Al
Glass/ITO/SiO/PEDOT:PSS/PVK:emitter/TPBI/LiF/Al
Glass/ITO/SiO/poly(vinyl-TPD)/PVK:emitter/TPBI/LiF/Al Where the phosphorescent emitter comprises a cyclometallated complex according to the present invention which emits blue light it is preferred that a wide band gap host material is used, such as a tetraarylsilane.

In a most preferred embodiment the phosphorescent emitter and host are combined in a molecule which may be small molecule, a dendrimer or a polymer.

Glass/ITO/PEDOT:PSS/combined host-emitter/TPBI/LiF/Al
Glass/ITO/poly(vinyl-TPD)/combined host-emitter/TPBI/LiF/Al
Glass/ITO/SiO/PEDOT:PSS/combined host-emitter/TPBI/LiF/Al
Glass/ITO/SiO/poly(vinyl-TPD)/combined host-emitter/TPBI/LiF/Al Organic optoelectronic devices may be prepared by any suitable method known to those skilled in the art. Typically the substrate will comprise a glass sheet upon which a layer of anode material, such as ITO, may be deposited by sputtering. The ITO or other anode material may, if required, be patterned using either additive methods during deposition, such as printing, or using subtractive methods following deposition, such as photolithography. The organic layers of the device may be deposited by vapour deposition, this is a particularly suitable method for the deposition of low molecular weight organic optoelectronic materials.

Where the organic optoelectronic materials are soluble they may be advantageously deposited by solution processing techniques. Solution processing techniques include selective methods of deposition such as screen printing and ink-jet printing and non-selective methods such as spin coating and doctor blade coating. Cyclometallated complexes of the present invention which incorporate host moieties are particularly suited to solution processing as such materials are not present in the form of a blend and therefore will not phase separate on deposition.

The cathode and any additional dielectric or electron transporting/hole blocking layers may be deposited using vapour deposition. Auxiliary layers and features may be included in the organic optoelectronic device as appropriate to improve charge injection or to facilitate patterning of the device.

EXAMPLES

Example 1

3,5-Dibromo-1-iso-butyl-1H-[1,2,4]triazole (Compound 1B)

A mixture of 3,5-dibromo-1H-[1,2,4]triazole (Zumbrunn, *Synthesis*, 1998, 1357) (1A) (440 mg, 1.94 mmol), potassium carbonate (483 mg, 3.49 mmol), iso-butylbromide (0.4 mL, 3.49 mmol), and N,N-dimethylformamide (5 mL) was heated at 103° C. under argon for 4 h. The mixture was allowed to cool to room temperature. Water (20 mL) was added and the mixture was extracted with ether (3×20 mL). The ether extracts were combined, washed with brine (1×30 mL), dried over anhydrous sodium sulphate, filtered and the solvent was completely removed to leave 1B as a pale yellow oil (548 mg, 100%); $^1$H (200 MHz; CDCl$_3$) 0.96 (6H, J 6.6 Hz, CH$_3$), 2.28 (1H, m, CH), and 3.94 (2H, d, J 7.4 Hz, CH$_2$); m/z [APCI$^+$] 280, 282, 284 (M$^+$).

Example 2

3-Bromo-1-iso-butyl-5-(2',4'-difluorophenyl)-1H-[1,2,4]triazole (Compound 1C)

A mixture of 1B (6.80 g, 24.0 mmol), 2,4-difluorophenylboronic acid (6.07 g, 38.5 mmol), tetrakis(triphenylphosphine)palladium(0) (833 mg, 0.721 mmol), aqueous sodium carbonate (2 M, 21 mL), ethanol (21 mL) and toluene (63 mL) was deoxygenated and heated at 103° C. under argon for 19 h. The mixture was allowed to cool to room temperature. The organic layer was separated. The aqueous layer was extracted with ether (3×30 mL). The organic layer and the ether extracts were combined, washed with brine (1×50 mL), and dried over anhydrous sodium sulphate and filtered. The solvents were completely removed to give 8.2 g of light yellow oil. The oil was purified by column chromatography over silica gel using a dichloromethane-light petroleum mixture (1:100 to 1:10) as eluent to give 1C (900 mg, 12%); $^1$H (200 MHz; CDCl$_3$) 0.80 (6H, d, J 6.6 Hz, CH$_3$), 2.26 (1H, m, CH), 3.84 (2H, d, J 8.0 Hz, CH$_2$), 6.92-7.14 (2H, m, ArH), and 7.45-7.60 (1H, m, ArH).

Example 3

[BDFIBTriazole]$_3$Ir (Compound 4B)

A mixture of 1C (470 mg, 1.49 mmol), iridium chloride tri-hydrate (131 mg, 0.371 mmol), water (2.0 mL) and 2-ethoxyethanol (6.0 mL) was heated at 130° C. under argon for 13 h before being cooled. The precipitate was separated from the mixture. The solid was washed with ethanol (8×3 mL) and light-petroleum (5×8 mL) and dried to give dichloro-bridged dimer 4A (262 mg, 82%) as a pale yellow solid; $^1$H (200 MHz; CDCl$_3$) 0.95-1.10 (24H, m, CH$_3$), 2.20-2.43 (4H, m, CH), 4.40-4.68 (8H, m, CH$_2$), 5.74 (4H, m, ArH), and 6.40 (4H, m, ArH).

A mixture of the iridium complex (4A) (180 mg, 0.210 mmol) and 1C (370 mg, 1.17 mmol) and silver trifluoromethanesulfonate (108 mg, 0.420 mmol) was heated at 156-160° C. for 38 h under argon. The reaction was then allowed to cool to room temperature. The mixture was dissolved in dichloromethane (~4 mL) and purified by column chromatography over silica gel using a dichloromethane-light petroleum mixture (1:30 to 1:8) as eluent to give a pale yellow solid of 4B as a mixture of isomers (232 mg, 97%); $^1$H (200 MHz; CDCl$_3$) 0.80-1.02 (18H, m, CH$_3$), 2.10-2.31 (3H, m, CH), 4.40 (6H, m, CH$_2$), 6.05 (3H, m, ArH), and 6.46 (3H, m, ArH); m/z [MALDI] 1133, 1135, 1136, 1137, 1138, 1139, 1140, 1141, 1142 (M$^+$). The photoluminescence spectrum of a neat film of complex 4B spin coated from a 9.5% solution in chloroform is shown in FIG. 1. The neat film shows a very good blue emission with clear vibronic structure giving peaks at 428, 450 and 490 nm.

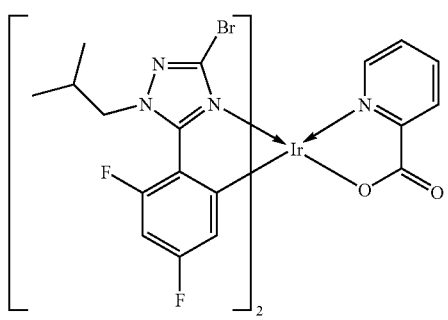

Example 4

(IBBrF$_2$PhTriazole)$_2$IrPic (Compound 4C, Shown Above)

A mixture of the iridium complex (4A) (28 mg, 0.033 mmol), picolinic acid (12 mg, 0.098 mmol), sodium carbonate (35 mg, 0.284 mmol) and 1,2-dichloroethane (2 mL) was heated at reflux under Ar$_{(g)}$ for 20 h. The dichloromethane (3 mL) and water (2 mL) were added. The organic layer was separated and the aqueous layer was extracted with dichloromethane (3×2 mL). The organic portions were combined and washed with brine (1×5 mL), dried (Na$_2$SO$_4$) and the solvent was removed. The residue was purified over silica gel using ethyl acetate-dichloromethane (0:1 to 2:1) as elute to give a yellowish solid 4C (31 mg, 100%); $^1$H (200 MHz; CDCl$_3$) 0.80-1.02 (12H, m, Me), 2.13-2.38 (2H, m, CH), 4.32-4.67 (4H, m, CH$_2$), 5.79 (1H, m, ArH), 6.10 (1H, m, ArH), 6.49 (2H, m, ArH), 7.41 (1H, m, PyH), 7.72 (1H, m, PyH), 7.93 (1H, m, PyH), and 8.31 (1H, m, PyH); m/z [APES$^+$] 942, 944, 946, 947, 948, 949 (MH$^+$).

Example 5

3,5-Dibromo-1-{3',5'-di[4"-(2'"-ethylhexyloxy)phenyl]benzyl}-1H-[1,2,4]triazole (Compound 3A of Scheme 3)

A mixture of the dibromo-triazole 1A (805 mg, 3.55 mmol), the 3,5-di[4'-(2"-ethylhexyloxy)phenyl]benzyl bromide (prepared as disclosed in WO 0159030) (2.67 g, 4.61 mmol), K$_2$CO$_3$ (896 mg, 6.48 mmol) and dried DMF (16 cm$^3$) was deoxygenated and then heated at a bath temperature of 98-108° C. under argon for 46 h. The mixture was allowed to cool to room temperature and poured into 70 cm$^3$ of water. The mixture was extracted with ether (4×30 cm$^3$). The ether extracts were combined, washed with water (2×40 cm$^3$), and brine (1×40 cm$^3$), and dried over anhydrous sodium sulphate. The solvents were completely removed to leave a yellow oil. The oil was purified by column chromatography over silica gel using DCM-light petroleum (0:1 to 1:10) as eluent to give 1.82 g (71%) of 3A as a white solid; $^1$H (400 MHz; CDCl$_3$) 0.91-1.02 (12H, m, 4×Me), 1.32-1.63 (16H, m, 8×CH$_2$), 1.72-1.83 (2H, m, 2×CH), 3.91 (4H, m, 2×ArOCH$_2$), 5.42 (2H, s, ArCH$_2$), 7.01 (4H, m, 4×ArCH), 7.42 (2H, m, 2×ArH), 7.54 (4H, m, 4×ArCH), and 7.70 (1H, m, ArH)

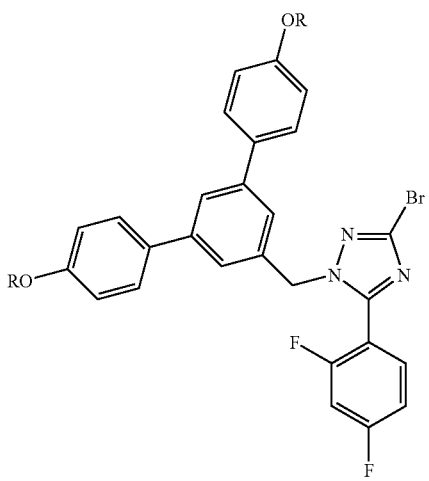

Example 6

3-Bromo-1-{3',5'-di[4"-(2'"-ethylhexyloxy)phenyl]benzyl}-5-(2',4'-difluorophenyl)-1H-[1,2,4]triazole (Compound 3B Shown Above)

A mixture of the dibromo-triazole 3A (375 mg, 0.517 mmol), the 2',4'-difluorophenyl boronic acid (146 mg, 0.93 mmol), tetrakis(triphenylphosphine)palladium(0) (42 mg, 0.036 mmol), 2 M Na$_2$CO$_{3(aq)}$ (0.3 cm$^3$), EtOH (0.3 cm$^3$) and toluene (1.0 cm$^3$) was deoxygenated and heated at reflux (with bath temperature of 110° C.) under argon for 5 days. The mixture was allowed to cool. Water (5 cm$^3$) and ether (10 cm$^3$) were added to the mixture. The organic layer was separated. The aqueous layer was extracted with ether (3×6 cm$^3$). The organic layer and the ether extracts were combined, washed with brine (1×19 cm$^3$), and dried over anhydrous sodium sulphate. The solvents were completely removed. The residue was purified by column chromatography over silica gel using DCM-light petroleum (0:1 to 1:10) as eluent to give 187 mg (48%) of 3B as a colourless oil; $^1$H (200 MHz; CDCl$_3$) 0.72-1.04 (12H, m, CH$_3$), 1.12-1.84 (18H, m, CH$_2$ & CH), 3.89 (4H, m, OCH$_2$), 5.37 (2H, s, ArCH$_2$), and 6.80-7.62 (14H, m, ArH).

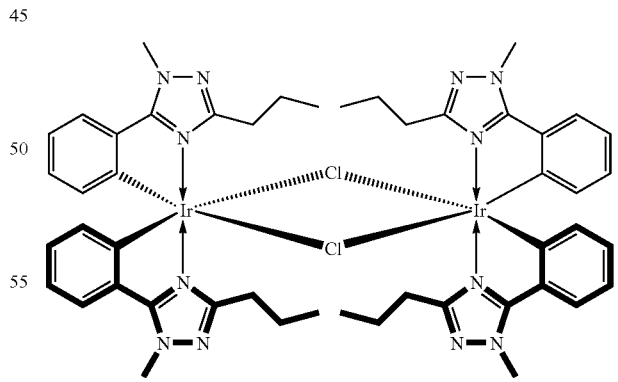

Example 7

(MePrPhTriazole)$_2$IrCl (Compound 6A Shown Above)

A mixture of the triazole ligand (MePrPhTriazole) (5C) (1.43 g, 7.09 mmol), iridium chloride trihydrate (1.00 g, 2.84 mmol), water (14 mL) and 2-EtOEtOH (40 mL) was heated at reflux under $N_{2(g)}$ for 13 h. The mixture was allowed to cool to room temperature. Water (48 mL) was added to the mixture to precipitate the yellow solid. The solid was filtered off and washed with water. The mixture was evaporated to dryness to give 1.50 g (84%) of brownish yellow solid of 6A was obtained; $^1$H (200 MHz; CDCl$_3$) 0.83 (12H, m, Me), 1.51-1.98 (8H, m, CH$_2$), 2.20-2.42 (4H, m, CH$_2$), 2.71-2.94 (4H, m, CH$_2$), 4.31 (12H, s, Me), 6.21 (4H, m, ArH), 6.66 (4H, m, ArH), 6.80 (4H, m, ArH), and 7.40 (4H, m, ArH).

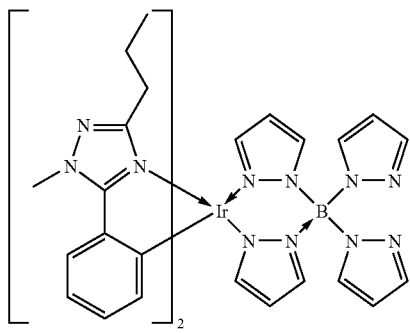

Example 8

(MePrPhTriazole)$_2$IrTPB (Compound 6D Shown Above)

A mixture of the iridium complex (6A) (250 mg, 0.398 mmol), tetrakis(1-pyrazolyl)borate (TPB) potassium salt (250 mg, 0.786 mmol) and dichloromethane (25 mL) was stirred at room temperature under $N_{2(g)}$ for 23 h. The solvent was removed and the mixture was purified over silica gel chromatography using ethyl acetate-light petroleum (1:10 to 1:3) as elute to give a yellow powder of (6D) (206 mg, 59%); $^1$H (400 MHz; CDCl$_3$) 0.68 (6H, m, Me), 1.21-1.28 (2H, m, CH$_2$), 1.36-1.58 (6H, m, CH$_2$), 4.23 (6H, s, Me), 6.12 (4H, m, PyrazolylH), 6.40, (2H, d, 7.6 Hz, ArH), 6.45 (2H, m, PyrazolylH), 6.71 (2H, m, PyrazolylH), 6.88 (2H, m, ArH), 7.00 (2H, m, ArH), 7.20 (2H, m, PyrazolylH), 7.53 (2H, d, 7.6 Hz, ArH), and 7.68 (2H, m, PyrazolylH). The photoluminescence quantum yield of a neat film of 6D spin coated from a solution of chloroform is 1%, having the CIE coordinates x=0.16, y=0.19.

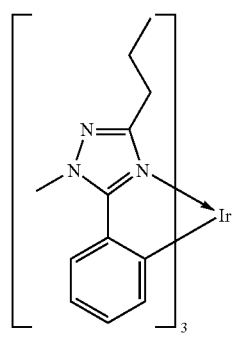

Example 9

(MePrPhTriazole)$_3$Ir (Compound 6B Shown Above)

A mixture of the iridium complex (6A) (370 mg, 0.589 mmol), the triazole ligand (MePrPhTriazole) (SC) (710 mg, 3.53 mmol) and silver triflate (303 mg, 1.18 mmol) was heated with oil bath temperature of 170° C. for 19 h under $N_{2(g)}$. The mixture was allowed to cool to room temperature and purified over silica gel using ethyl acetate-light petroleum (1:50 to 1:2) as elute to give a yellow powder of 6B (450 mg, 96%); $^1$H (400 MHz; CDCl$_3$) 0.69 (9H, t, 7.3 Hz, Me), 1.09-1.22 (3H, m, CH$_2$), 1.30-1.44 (3H, m, CH$_2$), 1.82-1.94 (3H, m, CH$_2$), 2.14-2.26 (3H, m, CH$_2$), 4.16 (9H, s, Me), 6.61 (3H, d, 7.5 Hz, ArH), 6.81 (3H, m, ArH), 6.90 (3H, m, ArH), and 7.52 (3H, d, 7.7 Hz, ArH). The photoluminescence quantum yield of a neat film of 6B spin coated from a solution of chloroform is 9%, having the CIE coordinates x=0.21, y=0.30.

Example 10

Electroluminescent Device

An organic electroluminescent device having the structure glass substrate/ITO/Compound 6B (100 nm)/TPBI (40 nm)/LiF (5 nm)/Ca (20 nm)/Al (100 nm) was prepared. When operated under a forward bias of 5V the device emitted blue light having the CIE coordinates x=0.21, y=0.31.

Example 11

Electroluminescent Device

Onto a glass substrate carrying an ITO anode was deposited a layer of PEDT/PSS (polyethylene dioxythiophene/polystyrene sulfonate available from H. C. Starck of Leverkusen, Germany) by spin-coating. An phosphorescent layer comprising the host material di(t-butyl)CBP, the phosphorescent compound 6B and, optionally, polymethylmethacrylate (PMMA) was deposited over the PEDT/PSS by spin-coating a mixture of the phosphorescent layer components from toluene solution. The quantity of compound 6B in the mixture was 10% by weight.

A cathode comprising a first layer of lithium fluoride and a second layer of aluminium was then deposited over the phosphorescent layer by vacuum evaporation. The level of PMMA in the phosphorescent layer was varied.

Example 12

Electroluminescent Device

Devices according to Example 11 were also formed using a layer of silicon oxide (SiO) in place of PEDT/PSS.

Example 13

Light Emission Characteristics of the Electroluminescent Devices

The devices of Examples 11 and 12 were tested to determine their CIE and quantum efficiency. The results are shown in Table 1 below. The ratio of di(t-butyl)CBP:PMMA:6B is a weight ratio.

TABLE 1

| Device structure | CIE-x | CIE-y | QE Max (%) |
|---|---|---|---|
| PEDT:PSS/di'Bu-CBP:6B (9:1) | 0.201 | 0.268 | 1.15 |
| PEDT:PSS/di'Bu-CBP:PMMA:6B (9:9:2) | 0.176 | 0.233 | 1.93 |
| SiO/di'Bu-CBP:PMMA:6B (9:9:2) | 0.176 | 0.284 | 1.26 |
| PEDT:PSS/di'Bu-CBP:PMMA:6B (13:5:2) | 0.186 | 0.245 | 1.62 |
| SiO/di'Bu-CBP:PMMA:6B (13:5:2) | 0.177 | 0.279 | 0.43 |
| PEDT:PSS/di'Bu-CBP:PMMA:6B (5:13:2) | 0.175 | 0.243 | 2.28 |
| SiO/CBP2:PMMA:PBIA (5:13:2) | 0.171 | 0.284 | 0.19 |

Example 14

Vacuum Evaporation of the Electroluminescent Layer

The process of Example 11 was followed except that the devices comprise the following structure:

Glass/ITO/SiO/NPD (optional)/combined host-emitter 6B/TPBI/LiF/Al

Both the hole transporting NPD layer, when present, and the combined host-emitter layer were formed by vacuum evaporation. The host materials used were CBP and MTDATA.

The best results (i.e. where emission from the host material was minimised) were obtained using mTDATA with the NPD layer present. A device having a hole transport layer of NPD and an electroluminescent layer of mTDATA:Compound 6B (9:1 ratio) gave a maximum quantum efficiency of 0.44%, CIE-x 0.175, CIE-y 0.232.

No doubt the teaching herein makes many other embodiments of, and effective alternatives to, the present invention apparent to a person skilled in the art. The present invention is not limited to the specific embodiments described herein but encompasses modifications which would be apparent to those skilled in the art and lying with the spirit and scope of the attached claims.

We claim:

1. An organic light-emitting device comprising a phosphorescent layer disposed between two electrodes, wherein said device has a CIE-y coordinate of less than 0.25, and wherein said phosphorescent layer comprises:
   (a) a cyclometallated complex comprising the structure of formula I:

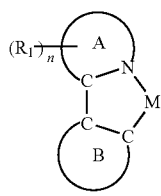

I wherein:
M is a d-block transition metal;
B is a five- or six-membered aryl or heteroaryl ring which is optionally substituted and optionally fused to one or more other aryl or heteroaryl rings;
A is a five- or six-membered heteroaryl ring comprising at least three nitrogen atoms;
$R_1$ is a group other than hydrogen;
n is zero or an integer equal to or greater than one; and
A and B are optionally fused or linked by one or more covalent bonds;
or
   (b) a cyclometallated complex comprising the structure of formula II:

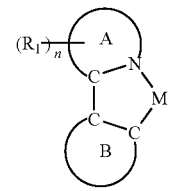

II wherein M is a d-block transition metal, A is a five- or six-membered heteroaryl ring which comprises at least three heteroatoms and which is optionally substituted or fused, B is a five- or six-membered aryl or heteroaryl ring which is optionally substituted or fused, n is greater than one and $R_1$ is a dendron or a solubilising group;
or
   (c) a polymer, which polymer comprises a cyclometallated complex, wherein the cyclometallated complex comprises the structure of formula I or formula II and is incorporated in a main chain or a side chain of the polymer.

2. An organic light-emitting device according to claim 1 wherein said device has a CIE-y coordinate of between 0.15 and 0.25.

3. An organic light-emitting device according to claim 1 wherein A is a five-membered ring.

4. An organic light-emitting device according to claim 3 wherein A is selected from the group consisting of triazole and tetrazole.

5. An organic light-emitting device according to claim 1 wherein A is a six-membered ring.

6. An organic light-emitting device according to claim 5 wherein A is a triazine.

7. An organic light-emitting device according to claim 1 wherein B is a five-membered ring.

8. An organic light-emitting device according to claim 7 wherein B is selected from the group consisting of thiophene, furan and pyrrole.

9. An organic light-emitting device according to claim 1 wherein B is a six-membered ring.

10. An organic light-emitting device according to claim 9 wherein B is selected from the group consisting of benzene, pyridine, pyrazine and pyrimidine.

11. An organic light-emitting device according to claim 1 wherein M is selected from the group consisting of iridium, rhodium, palladium, platinum, gold, osmium and ruthenium.

12. An organic light-emitting device according to claim 11 wherein M is selected from the group consisting of iridium and platinum.

13. An organic light-emitting device according to claim 1 wherein the cyclometallated complex is homoleptic.

14. An organic light-emitting device according to claim 1 wherein the cyclometallated complex is heteroleptic.

15. An organic light-emitting device according to claim 14 wherein said complex further comprises a ligand selected from the group consisting of picolinates, acetylacetates, phosphines, pyridine and pyridine derivatives, carbonyl, nitrile, isonitriles, halides and tetrakis(1-pyrazolyl)borates.

16. An organic light-emitting device according to claim 1 wherein $R_1$ is greater than or equal to one and at least one group $R_1$ is an electron-donating group.

17. An organic light-emitting device according to claim 16 wherein n is greater than one.

18. An organic light-emitting device according to claim 16 wherein said electron-donating group is selected from the group consisting of alkylamino, arylamino, alkyl, alkoxy, aryl and carbazole groups.

19. An organic light-emitting device according to claim 1 wherein said ring B is substituted with at least one electron-withdrawing group.

20. An organic light-emitting device according to claim 19 wherein said electron-withdrawing group is selected from the group consisting of halogen atoms, haloalkyl groups, sulfoxides and sulfones.

21. An organic light-emitting device according to claim 20 wherein said electron-withdrawing group is selected from fluorine or perfluorinated $C_{1-6}$ haloalkyl groups.

22. An organic light-emitting device according to claim 1 wherein A comprises a triazole group substituted with at least one group $R_1$ which is an electron donating group, B comprises a phenyl group substituted with at least one fluorine or fluorinated group and said d-block transition metal is iridium.

23. An organic light-emitting device according to claim 1 wherein ring A is substituted with at least one group $R_1$ which is a dendron.

24. An organic light-emitting device according to claim 23 wherein said dendron comprises a carbazole moiety or a triarylamine moiety.

25. An organic light-emitting device according to claim 23 wherein said dendron comprises a 1,3,5-substituted phenyl moiety.

26. An organic light-emitting device according to claim 1 wherein ring B is substituted with at least one dendron.

27. An organic light-emitting device according to claim 1 wherein said phosphorescent layer comprises a polymer, and wherein the cyclometallated complex is incorporated into the main chain of the polymer.

28. An organic light-emitting device according to claim 27 wherein said polymer further comprises a carbazole or triarylamine group.

29. An organic light-emitting device according to claim 1 wherein said phosphorescent layer comprises a polymer, and wherein the cyclometallated complex is pendant to the main chain of the polymer.

30. An organic light-emitting device according to claim 1 wherein the phosphorescent layer comprises an organic host material.

31. An organic light-emitting device according to claim 30 wherein the organic host material is di(t-butyl)CBP which has the following structure:

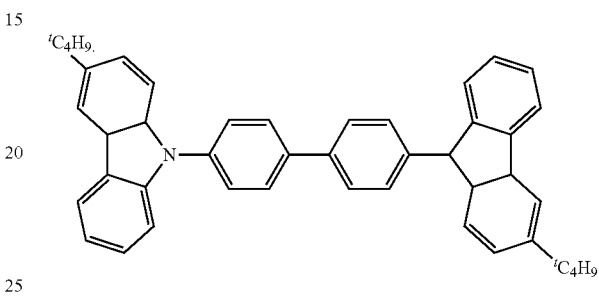

32. An organic light-emitting device according to claim 30 wherein the phosphorescent layer further comprises a diluent compound.

33. An organic light-emitting device according to claim 32 wherein the diluent compound is polymethylmethacrylate (PMMA).

34. An organic light-emitting device according to claim 32 wherein the diluent compound is present in an amount of from 30 to 80% by weight.

* * * * *

UNITED STATES PATENT AND TRADEMARK OFFICE
CERTIFICATE OF CORRECTION

| | | |
|---|---|---|
| PATENT NO. | : 8,216,699 B2 | Page 1 of 1 |
| APPLICATION NO. | : 12/646529 | |
| DATED | : July 10, 2012 | |
| INVENTOR(S) | : Burn et al. | |

It is certified that error appears in the above-identified patent and that said Letters Patent is hereby corrected as shown below:

On the Title page, Item (73) Assignee, the following should be added

-- The University Court of the University of St. Andrews --

Signed and Sealed this
Twenty-second Day of October, 2013

Teresa Stanek Rea
*Deputy Director of the United States Patent and Trademark Office*